United States Patent [19]

Matsuo et al.

[11] Patent Number: 5,571,810

[45] Date of Patent: Nov. 5, 1996

[54] THIOPHENE DERIVATIVES

[75] Inventors: Masaaki Matsuo, Toyonaka; Kiyoshi Tsuji, Kishiwada; Nobukiyo Konishi, Nagaokakyo; Katsuya Nakamura, Takatsuki, all of Japan

[73] Assignee: Fujisawa Pharmaceutical Co., Ltd., Osaka, Japan

[21] Appl. No.: 422,545

[22] Filed: Apr. 13, 1995

Related U.S. Application Data

[63] Continuation of Ser. No. 955,739, Dec. 3, 1992, abandoned.

[30] Foreign Application Priority Data

Nov. 6, 1990 [GB] United Kingdom ............... 9012936

[51] Int. Cl.$^6$ ............... A61K 31/535; A61K 31/38; A61K 31/495; A61K 31/42

[52] U.S. Cl. ............... 514/231.5; 514/255; 514/422; 514/378; 514/380; 514/365; 514/369; 514/370; 514/438; 514/445; 514/447; 544/146; 544/374; 548/202; 548/203; 548/243; 548/244; 548/245; 548/246; 548/247; 548/527; 549/68; 549/75; 549/78

[58] Field of Search ............... 549/75, 68, 78; 514/438, 445, 447, 231.5, 255, 422, 378, 380, 365, 369, 370; 548/202, 203; 544/146, 374

[56] References Cited

U.S. PATENT DOCUMENTS

| | | | |
|---|---|---|---|
| 4,292,446 | 9/1981 | Riley | 564/221 |
| 4,432,974 | 2/1984 | Haber | 424/184 |
| 4,645,777 | 2/1987 | Burkart et al. | 514/444 |
| 4,749,712 | 6/1988 | Haber | 514/438 |

FOREIGN PATENT DOCUMENTS

| | | |
|---|---|---|
| 0024042 | 2/1981 | European Pat. Off. . |
| 0055470 | 7/1982 | European Pat. Off. . |
| 0055471 | 7/1982 | European Pat. Off. . |
| 0087629 | 9/1983 | European Pat. Off. . |

OTHER PUBLICATIONS

Chem. Ber. vol. 116, pp. 3112–3124 (1983); F. Vögtle et al. "Neue helicale Moleküle, IX. Synthesen, Enantiomerentrennungen, . . . ".

Chemical Abstracts vol. 80, p. 355, 4789p; "Reactions of (β–chloro–vinyl)aldehydes III. Synthesis and properties . . . ".

Chemical Abstracts vol. 90, pp. 614–615, 87343u; "Synthesis and biological activity of 5–arylthiophene–2–carboxylic acid . . . ".

Research Disclosure, vol. 266, Jun. 1986, pp. 323–324, No. 26615; W. W. Wilkerson "Antiinflammatory 2–cyano–4, 5–diarylheterocycles".

*Primary Examiner*—José G. Dees
*Assistant Examiner*—Mary C. Cebulak
*Attorney, Agent, or Firm*—Oblon, Spivak, McClelland, Maier & Neustadt, P.C.

[57] ABSTRACT

This invention relates to new thiophene derivatives having antiinflammatory and analgesic activities and represented by the general formula [I]:

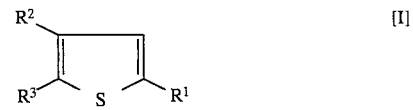

wherein
- $R^1$ is hydrogen, halogen, cyano, substituted lower alkyl, substituted or unsubstituted lower alkenyl, acyl, nitro, substituted or unsubstituted amino, sulfo, substituted or unsubstituted sulfamoyl, N-containing heterocyclicsulfonyl, hydoxy, substituted or unsubstituted heterocyclic group,
- $R^2$ is substituted or unsubstituted aryl, and
- $R^3$ is substituted or unsubstituted aryl, provided that $R^3$ is aryl substituted with substituent(s) selected from the group consisting of amino, mono(lower)-alkylamino, acylamino, lower alkyl(acyl)amino and sulfamoyl when $R^1$ is hydrogen, halogen or cyano, and pharmaceutically acceptable salts thereof, to processes for the preparation thereof and to a pharmaceutical composition comprising the same.

8 Claims, No Drawings

THIOPHENE DERIVATIVES

This application is a Continuation of application Ser. No. 07/955,739, filed on Dec. 3, 1992, now abandoned, which was filed as International Application No. PCT/JP91/00744, on May 31, 1991.

TECHNICAL FIELD

This invention relates to new thiophene derivatives and pharmaceutically acceptable salts thereof which are useful as a medicament.

BACKGROUND ART

Some thiophene derivatives having antiinflammatory and analgesic activities have been known as described, for example, in European Patent Application Publication Nos. 24 042 and 87 629, U.S. Pat. No. 4,749,712 and Research Disclosure 266015.

DISCLOSURE OF INVENTION

The present invention relates to new thiophene derivatives and pharmaceutically acceptable salts thereof.

More particularly, it relates to new thiophene derivatives and pharmaceutically acceptable salts thereof which have antiinflammatory and analgesic activities, to processes for preparation thereof, to a pharmaceutical composition comprising the same, and to methods of using the same therapeutically in the treatment and/or prevention of inflammatory conditions and various pains, collagen diseases, autoimmune diseases and various immunity diseases in human beings or animals, and more particularly to methods for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition [e.g. conjunctivitis, etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Chrohn's disease, atropic gastritis, gastritis varialoforme, ulcerative colitis, coeliac disease, regional ileitis, irritable bowel syndrome, etc.], gingivitis, inflammation, pain and tumescence after operation or injury, pyresis, pain and other conditions associated with inflammation, particularly those in which lipoxygenase and cyclooxygenase products are a factor, systemic lupus erythematosus, scleroderma, polymyositis, periarteritis nodosa, rheumatic fever, Sjögren's syndrome, Behcet disease, thyroiditis, type I diabetes, naphrotic syndrome, aplastic anemia, myasthenia gravis, uveitis contact dermatitis, psoriasis, Kawasaki disease, sarcoidosis, Hodgkin's disease, and the like.

One object of this invention is to provide new and useful thiophene derivatives and pharmaceutically acceptable salts thereof which possess antiinflammatory and analgesic activities.

Another object of this invention is to provide processes for the preparation of said thiophene derivatives and salts thereof.

A further object of this invention is to provide a pharmaceutical composition comprising, as an active ingredient, said thiophene derivatives and pharmaceutically acceptable salts thereof.

Still further object of this invention is to provide a therapeutical method for the treatment and/or prevention of inflammatory conditions, various pains, and the other diseases mentioned above, using said thiophene derivatives and pharmaceutically acceptable salts thereof.

The object thiophene derivatives of this invention are new and can be represented by the following general formula [I]:

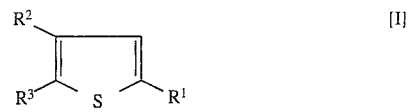

wherein $R^1$ is hydrogen; halogen; cyano; lower alkyl substituted with substituent(s) selected from the group consisting of halogen, hydroxy, amino, acylamino, lower alkylamino, lower alkyl(acyl)amino, acyl, aryl optionally substituted with hydroxy, a heterocyclic group, hydroxyimino and lower alkoxyimino; lower alkenyl optionally substituted with cyano; acyl; nitro; amino optionally substituted with substituent(s) selected from the group consisting of acyl and lower alkylsulfonyl; sulfo; sulfamoyl optionally substituted with substituent(s) selected from the group consisting of lower alkyl, halo(lower)alkyl, aryl, hydroxy, lower alkylamino(lower)alkyl, a heterocyclic group and (esterified carboxy)lower alkyl; N-containing heterocyclicsulfonyl; hydroxy; or a heterocyclic group optionally substituted with substituent(s) selected from the group consisting of hydroxy, oxo, amino and lower alkylamino;

$R^2$ is aryl optionally substituted with substituent(s) selected from the group consisting of halogen, lower alkoxy, lower alkylthio, lower alkylsulfinyl, lower akylsulfonyl, nitro, amino, sulfamoyl and lower alkylsulfonylamino; and $R^3$ is aryl optionally substituted with substituent(s) selected from the group consisting of halogen, lower alkoxy, lower alkylthio, lower alkylsulfinyl, lower alkylsulfonyl, nitro, amino, lower alkylamino, acylamino, lower alkyl(acyl)amino, lower alkylsulfonylamino and sulfamoyl;

provided that $R^3$ is aryl substituted with substituent(s) selected from the group consisting of amino, mono(lower)alkylamino, acylamino, lower alkyl(acyl)amino and sulfamoyl when $R^1$ is hydrogen, halogen or cyano, and pharmaceutically acceptable salts thereof.

The object compound [I] or its salt can be prepared by the following processes.

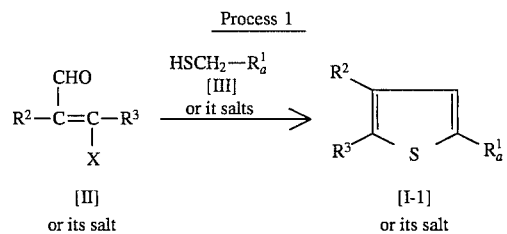

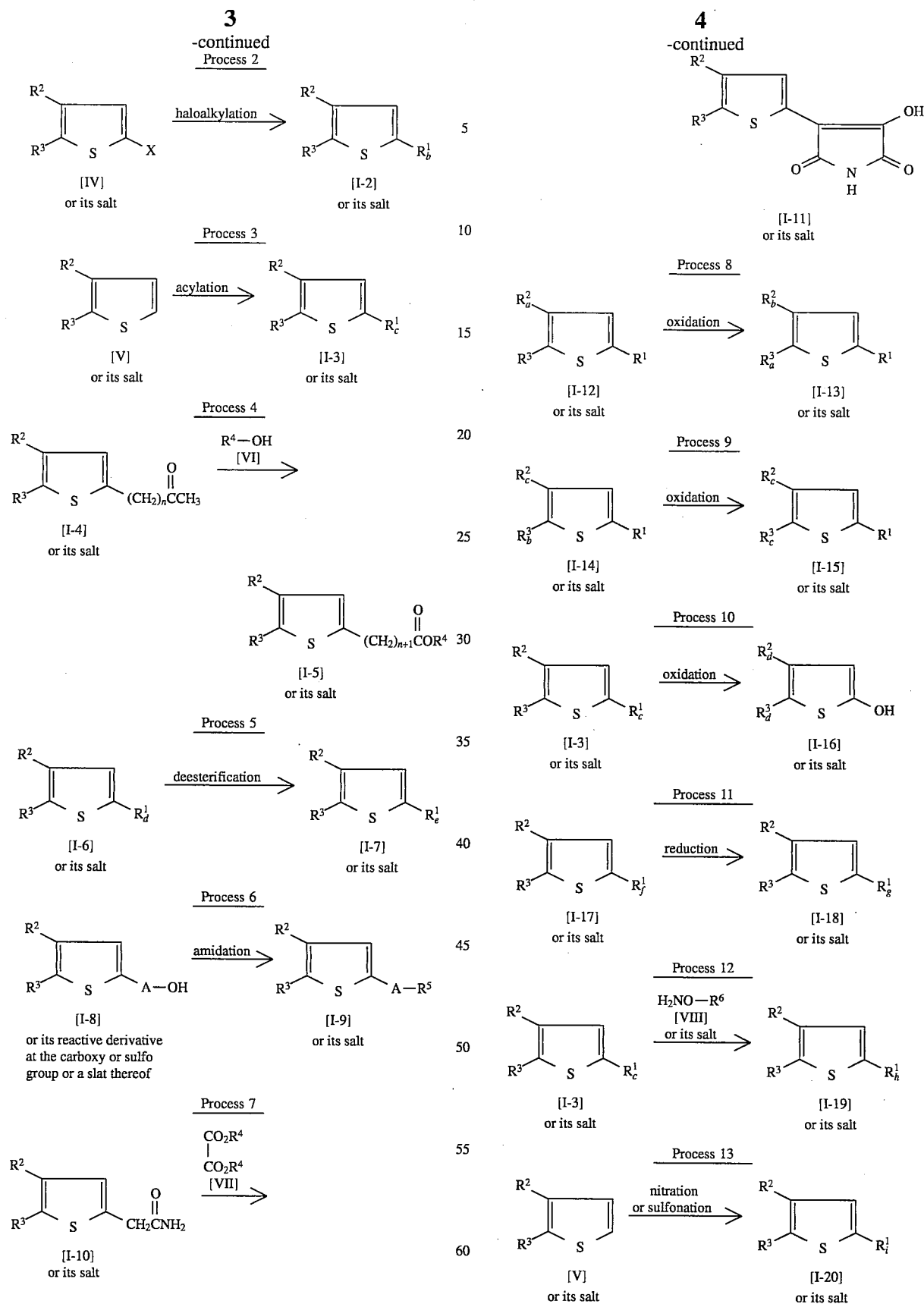

5
-continued

Process 14

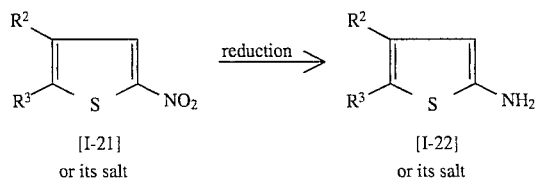

[I-21] or its salt → [I-22] or its salt

Process 15

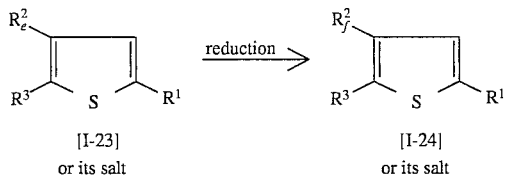

[I-23] or its salt → [I-24] or its salt

Process 16

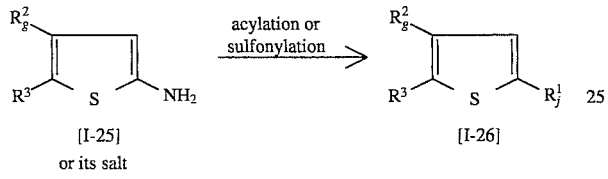

[I-25] or its salt → [I-26]

Process 17

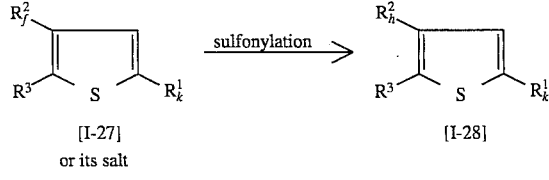

[I-27] or its salt → [I-28]

Process 18

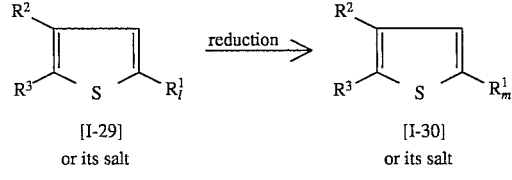

[I-29] or its salt → [I-30] or its salt

Process 19

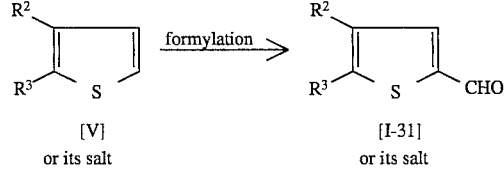

[V] or its salt → [I-31] or its salt

Process 20

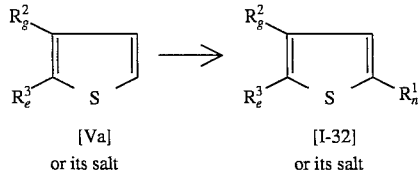

[Va] or its salt → [I-32] or its salt

6
-continued

Process 21

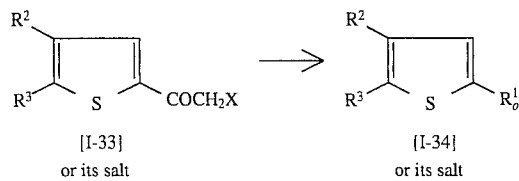

[I-33] or its salt → [I-34] or its salt

Process 22

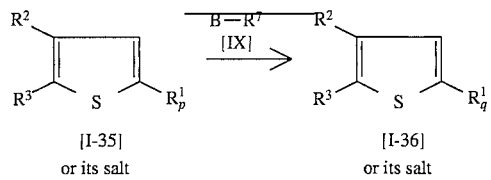

[I-35] or its salt → [I-36] or its salt

Process 23

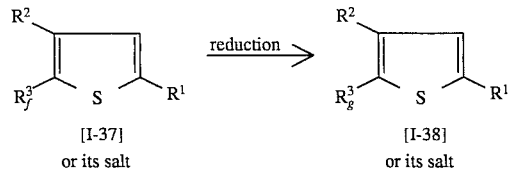

[I-37] or its salt → [I-38] or its salt

Process 24

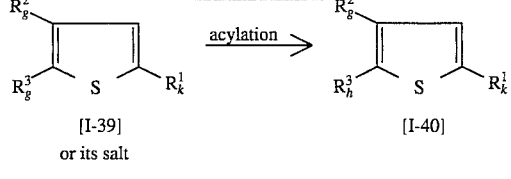

[I-39] or its salt → [I-40]

Process 25

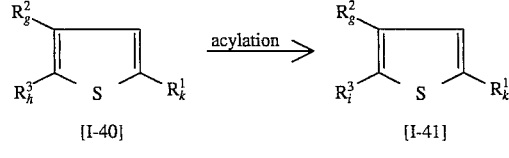

[I-40] → [I-41]

Process 26

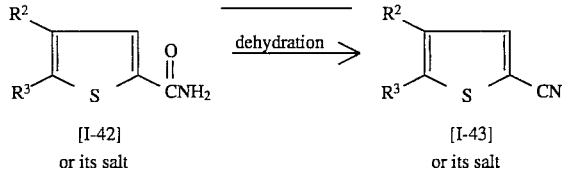

[I-42] or its salt → [I-43] or its salt

Process 27

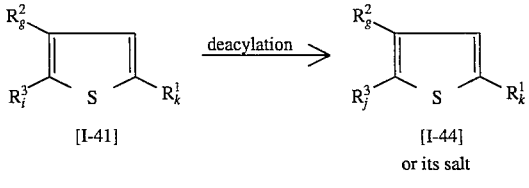

[I-41] → [I-44] or its salt

Process 28

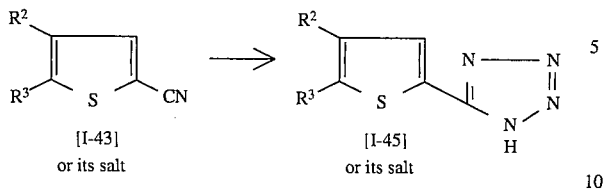

[I-43] or its salt → [I-45] or its salt wherein $R^1$ $R^2$ and $R^3$ are each as defined above;

$R_a^1$ is cyano or acyl;

X is halogen;

$R_b^1$ is halo(lower)alkyl;

$R_c^1$ is lower alkanoyl optionally substituted with halogen; or aroyl optionally substituted with hydroxy;

n is an integer of 0 to 6;

$R^4$ is lower alkyl;

$R_d^1$ is lower alkyl substituted with esterified carboxy; esterified carboxy; or optionally substituted with lower alkyl;

$R_e^1$ is lower alkyl substituted with carboxy; (esterified carboxy)lower alkylcarbamoyl carboxy; or carboxy-(lower)alkylcarbamoyl optionally substituted with lower alkyl;

A is —$(CH_2)_nCO$— or —$SO_2$—;

$R^5$ is amino optionally substituted with substituent(s) selected from the group consisting of lower alkyl, halo(lower)alkyl, aryl, hydroxy, lower alkylamino(lower)alkyl, a heterocyclic group and (esterified carboxy)lower alkyl; or N-containing heterocyclic group;

$R_a^2$ is lower alkylthio-substituted aryl optionally substituted with substituent(s) selected from the group consisting of halogen, lower alkoxy, nitro, amino, sulfamoyl and lower alkylsulfonylamino;

$R_a^3$ is aryl optionally substituted with substituent(s) selected from the group consisting of halogen, lower alkoxy, lower alkylsulfinyl, lower alkylsulfonyl, nitro, amino, lower alkylamino, acylamino, lower alkyl(acyl)amino and sulfamoyl;

$R_b^2$ is lower alkylsulfinyl- or lower alkylsulfonyl-substituted aryl optionally substituted with substituent(s) selected from the group consisting of halogen, lower alkoxy, nitro, amino, sulfamoyl and lower alkylsulfonylamino;

$R_c^2$ is aryl optionally substituted with substituent(s) selected from the group consisting of halogen, lower alkoxy, nitro, amino, sulfamoyl and lower alkylsulfonylamino;

$R_b^3$ is lower alkylthio-substituted aryl optionally substituted with substituent(s) selected from the group consisting of halogen, lower alkoxy, nitro, amino, lower alkylamino, acylamino, lower alkyl(acyl)amino and sulfamoyl;

$R_c^3$ is lower alkylsulfinyl- or lower alkylsulfonyl-substituted aryl optionally substituted with substituent(s) selected from the group consisting of halogen, lower alkoxy, nitro, amino, lower alkylamino, acylamino, lower alkyl(acyl)amino and sulfamoyl;

$R_d^2$ is aryl optionally substituted with substituent(s) selected from the group consisting of halogen, lower alkoxy, lower alkylsulfonyl, nitro, amino, sulfamoyl and lower alkylsulfonylamino;

$R_d^3$ is aryl optionally substituted with substituent(s) selected from the group consisting of halogen, lower alkoxy, lower alkylsulfonyl, nitro, amino, lower alkylamino, acylamino, lower alkyl(acyl)amino and sulfamoyl;

$R_f^1$ is carboxy; esterified carboxy; lower alkyl substituted with carboxy or esterified carboxy; or lower alkanoyl optionally substituted with halogen;

$R_g^1$ is hydroxy(lower)alkyl optionally substituted with halogen;

$R_h^1$ is lower alkoxyimino(lower)alkyl optionally substituted with halogen; or lower alkyl substituted with hydroxyimino and aryl optionally substituted with hydroxy;

$R^6$ is hydrogen or lower alkyl;

$R_i^1$ is nitro or sulfo;

$R_e^2$ is nitro-substituted aryl optionally substituted with substituent(s) selected from the group consisting of halogen, lower alkoxy, lower alkylthio, lower alkylsulfinyl, lower alkylsulfonyl, sulfamoyl and lower alkylsulfonylamino;

$R_f^2$ is amino-substituted aryl optionally substituted with substituent(s) selected from the group consisting of halogen, lower alkoxy, lower alkylthio, lower alkylsulfinyl, lower alkylsulfonyl, sulfamoyl and lower alkylsulfonylamino;

$R_g^2$ is aryl optionally substituted with substituent(s) selected from the group consisting of halogen, lower alkoxy, lower alkylthio, lower alkylsulfinyl, lower alkylsulfonyl, nitro, sulfamoyl and lower alkylsulfonylamino;

$R_j^1$ is amino substituted with substituent(s) selected from the group consisting of acyl and lower alkylsulfonyl;

$R_k^1$ is hydrogen halogen; cyano; lower alkyl substituted with substituent(s) selected from the group consisting of halogen, acylamino, lower alkyl(acyl)amino, acyl, aryl, a heterocyclic group and lower alkoxyimino; lower alkenyl optionally substituted with cyano; acyl; nitro; amino substituted with substituent(s) selected from the group consisting of acyl and lower alkylsulfonyl; sulfo; sulfamoyl optionally substituted with substituent(s) selected from the group consisting of lower alkyl, halo(lower)alkyl, aryl, a heterocyclic group and (esterified carboxy)lower alkyl; N-containing heterocyclicsulfonyl; or a heterocyclic group optionally substituted with oxo;

$R_h^2$ is lower alkylsulfonylamino-substituted aryl optionally substituted with substituent(s) selected from the group consisting of halogen, lower alkoxy, lower alkylthio, lower alkylsulfinyl, lower alkylsulfonyl and sulfamoyl;

$R_l^1$ is N-containing heterocycliccarbonyl; carbamoyl optionally substituted with lower alkyl; or lower alkyl substituted with carbamoyl optionally substituted with lower alkyl;

$R_m^1$ is lower alkyl substituted with N-containing heterocyclic group, amino or lower alkylamino; $R_e^3$ is aryl optionally substituted with substituent(s) selected from the group consisting of halogen, lower alkoxy, lower alkylthio, lower alkylsulfinyl, lower alkylsulfonyl, nitro, acylamino, lower alkyl(acyl)amino, lower alkylsulfonylamino and sulfamoyl;

$R_n^1$ is sulfamoyl optionally substituted with substituent(s) selected from the group consisting of lower alkyl, halo(lower)alkyl, aryl, hydroxy, lower alkylamino(lower)alkyl, a heterocyclic group and (esterified carboxy-)lower alkyl; or N-containing heterocyclicsulfonyl;

$R_o^1$ is thiazolyl substituted with amino or lower alkylamino;

$R_p^1$ is lower alkanoyl;

$R_q^1$ is lower alkenyl optionally substituted with cyano;

B is di-esterified phosphono or substituted phosphonium salt; and $R^7$ is lower alkyl optionally substituted with cyano;

$R_f^3$ is nitro-substituted aryl optionally substituted with substituent(s) selected from the group consisting of halogen, lower alkoxy, lower alkylthio, lower alkylsulfinyl, lower alkylsulfonyl, lower alkylamino, acylamino, lower alkyl(acyl)amino and sulfamoyl;

$R_g^3$ is amino-substituted aryl optionally substituted with substituent(s) selected from the group consisting of halogen, lower alkoxy, lower alkylthio, lower alkylsulfinyl, lower alkylsulfonyl, lower alkylamino, acylamino, lower alkyl(acyl)amino and sulfamoyl;

$R_h^3$ is acylamino-substituted aryl optionally substituted with substituent(s) selected from the group consisting of halogen, lower alkoxy, lower alkylthio, lower alkylsulfinyl, lower alkylsulfonyl, lower alkyl(acyl)amino and sulfamoyl;

$R_i^3$ is lower alkyl(acyl)amino-substituted aryl optionally substituted with substituent(s) selected from the group consisting of halogen, lower alkoxy, lower alkylthio, lower alkylsulfinyl, lower alkylsulfonyl and sulfamoyl; and $R_j^3$ is mono(lower)alkylamino-substituted aryl optionally substituted with substituent(s) selected from the group consisting of halogen, lower alkoxy, lower alkylthio, lower alkylsulfinyl, lower alkylsulfonyl and sulfamoyl.

In the above and subsequent description of the present specification, suitable examples of the various definitions to be included within the scope of the invention are explained in detail in the following. The term "lower" is intended to mean a group having 1 to 6 carbon atom(s), unless otherwise provided.

The lower moiety in the term "lower alkenyl" is intended to mean a group having 2 to 6 carbon atoms.

Suitable "lower alkyl" and lower alkyl moiety in the terms "lower alkylamino", "lower alkyl(acyl)amino", "lower alkylsulfonyl", "lower alkylthio", "lower alkylsulfinyl" and "lower alkylsulfonylamino" may be straight or branched one such as methyl, ethyl, propyl, isopropyl, butyl, isobutyl, tert-butyl, pentyl, hexyl or the like, in which preferable one is methyl or ethyl The lower alkyl group for $R^1$ may be substituted with substituent(s) as mentioned above, wherein the preferable number of the substituent(s) is 1 or 2.

Suitable "aryl" may be phenyl, naphthyl, phenyl substituted with lower alkyl [e.g. tolyl, xylyl, mesityl, cumenyl, di(tert-butyl)phenyl, etc.] and the like, in which preferable one is phenyl.

The aryl group for $R^2$ may be substituted with 1 to 5 substituent(s) as mentioned above and the aryl group for $R^3$ may be substituted with 1 to 5 substituent(s) as stated above, wherein the preferable number of the substituent(s) is 1 or 2.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 6-membered heteromonocyclic group containing 1 to 4 nitrogen atoms [e.g. pyrrolidinyl, imidazolidinyl, piperidino, piperazinyl, etc.]; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.;

unsaturated 3 to 6-membered heteromonocyclic group containing an oxygen atom, for example, pyranyl, furyl, etc.;

unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g., thiazolidinyl, etc.];

unsaturated condensed heterocyclic group containing 1 to 2 sulfur atoms and 1 to 3 nitrogen atoms [e.g., benzothiazolyl, benzothiadiazolyl, etc.] and the like. Said "heterocyclic group" may have 1 to 3 substituents such as lower alkyl as exemplified above, hydroxy, oxo, amino and lower alkylamino.

Preferable one is lower alkyl substituted with a heterocyclic group for $R^1$ is pyrrolidinylmethyl.

Preferable one in a heterocyclic group optionally substituted with substituent(s) selected from the group consisting of hydroxy, oxo, amino and lower alkylamino for $R^1$ is 4-hydroxy-2,5-dioxo-3-pyrrolin-3-yl, 2-aminothiazol-4-yl or 2-methylaminothiazol-4-yl.

Suitable "halogen" may be fluorine, chlorine, bromine and iodine, in which preferable one is fluorine or chlorine.

Suitable "acyl" and acyl moiety in the terms "acylamino" and "lower alkyl(acyl)amino" may be carboxy; esterified carboxy; carbamoyl optionally substituted with substituent(s) selected from the group consisting of lower alkyl, halo(lower)alkyl, aryl, hydroxy, lower alkylamino(lower)alkyl, a heterocyclic group, (esterified carboxy)lower alkyl and carboxy(lower)alkyl [e.g. lower alkyl-carbamoyl; arylcarbamoyl; carbamoyl substituted with a heterocyclic group, (esterified carboxy)lower alkyl or carboxy(lower)alkyl; lower alkylcarbamoyl substituted with hydroxy, lower alkylamino, (esterified carboxy)lower alkyl or carboxy(lower)alkyl; etc.]; lower alkanoyl; aroyl; a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like.

The lower alkyl-carbamoyl may be substituted with halogen or unsubstituted one such as methylcarbamoyl, ethylcarbamoyl, propylcarbamoyl, dimethylcarbamoyl, 2,2,2-trifluoroethylcarbamoyl or the like.

The aryl-carbamoyl may be phenylcarbamoyl, naphthylcarbamoyl, tolylcarbamoyl, xylylcarbamoyl, mesitylcarbamoyl, Cumenylcarbamoyl, and the like, in which preferable one is phenylcarbamoyl.

The carbamoyl substituted with a heterocyclic group may be one substituted with a heterocyclic group as mentioned above, in which preferable one is tetrazolylcarbamoyl.

The carbamoyl substituted with (esterified carboxy)lower alkyl may be methoxycarbonylmethylcarbamoyl, methoxycarbonylethylcarbamoyl, ethoxycarbonylmethylcarbamoyl, ethoxycarbonylethylcarbamoyl, benzyloxycarbonylmethylcarbamoyl and the like.

The carbamoyl substituted with carboxy(lower)alkyl may be carboxymethylcarbamoyl, carboxyethylcarbamoyl and the like.

The lower alkylcarbamoyl substituted with hydroxy may be N-hydroxy-N-methylcarbamoyl, N-ethyl-N-hydroxycarbamoyl, N-hydroxy-N-propylcarbamoyl, N-hydroxy-N-isopropylcarbamoyl and the like, in which preferable one is N-hydroxy-N-methylcarbamoyl.

The lower alkylcarbamoyl substituted with lower alkylamino may be methylaminomethylcarbamoyl, dimethylaminomethylcarbamoyl, dimethylaminoethylcarbamoyl, diethylaminoethylcarbamoyl, isopropylaminomethylcarbamoyl, isopropylaminoisobutylcarbamoyl and the like, in which preferable one is dimethylaminoethylcarbamoyl.

The lower alkylcarbamoyl substituted with (esterified carboxy)lower alkyl may be (methoxycarbonylmethyl)ethycarbamoyl, (ethoxycarbonylmethyl)methylcarbamoyl, (benzyloxycarbonylmethyl)methylcarbamoyl, (benzyloxycarbonylethyl)ethylcarbamoyl and the like, in which preferable one is (ethoxycarbonylmethyl)methylcarbamoyl.

The lower alkylcarbamoyl substituted with carboxy(lower)alkyl may be (carboxymethyl)ethylcarbamoyl, (carboxymethyl)methylcarbamoyl, (carboxyethyl)ethylcarbamoyl and the like, in which preferable one is (carboxymethyl)methylcarbamoyl.

The lower alkanoyl may be substituted or unsubstituted one such as formyl, acetyl, propionyl, butyryl, isobutyryl, valeryl, isovaleryl, pivaloyl, hexanoyl, trifluoroacetyl or the like, in which preferable one is formyl, acetyl, propionyl or trifluoroacetyl.

The aroyl may be benzoyl, naphthoyl, toluoyl, di(tert-butyl)benzoyl and the like and the aryl in said aroyl may be substituted with hydroxy.

The heterocyclic moiety in the term "a heterocycliccarbonyl" may be one mentioned above as a heterocyclic group and preferable one in said heterocycliccarbonyl is morpholinocarbonyl, pyrrolidinylcarbonyl or methylpiperazinylcarbonyl.

Suitable "lower alkoxy" and lower alkoxy moiety in term "lower alkoxyimino" may be methoxy, ethoxy, propoxy, isopropoxy, butoxy and the like, in which preferable one is methoxy.

Preferable "lower alkyl substituted with halogen" is trifluoromethyl or pentafluoroethyl.

Preferable "aryl substituted with hydroxy" is di(tert-butyl)hydroxyphenyl.

Suitable "lower alkenyl" may be a straight or branched one such as vinyl, allyl, isopropenyl, propenyl, butenyl, pentenyl or the like, in which preferable one is isopropenyl. Said lower alkenyl may be substituted with cyano.

Suitable "lower alkylamino" may be mono or di(lower alkyl)amino such as methylamino, ethylamino, dimethylamino, diethylamino or the like.

Suitable "sulfamoyl substituted with lower alkyl" may be methylsulfamoyl, ethylsulfamoyl, isopropylsulfamoyl, dimethylsulfamoyl, diethylsulfamoyl and the like, in which preferable one is methylsulfamoyl or dimethylsulfamoyl.

Suitable ester moiety in the term "di-esterified phosphono" can be referred to the ester moiety as exemplified for "esterified carboxy".

In this respect, the ester group of the di-esterified phosphono may be the same or different.

Suitable "substituted phosphonium salt" can be referred to the phosphonium salt conventionally used in the Wittig reaction [e.g. triphenylphosphonium bromide, tri(n-butyl)phosphonium chloride, etc.].

Suitable pharmaceutically acceptable salts of the object compound [I] are conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a salt with an amino acid [e.g. arginine salt, aspartic acid salt, glutamic acid salt, etc.], a metal salt such as an alkali metal salt [e.g. sodium salt, potassium salt, etc.] and an alkaline earth metal salt [e.g. calcium salt, magnesium salt, etc.], an ammonium salt, an organic base addition salt [e.g. trimethylamine salt, triethylamine salt, etc.] and the like.

The processes for preparing the object compound [I] are explained in detail in the following.

Process 1

The compound [I-1] or its salt can be prepared by reacting a compound [II] or its salt with a compound [III] or its salt.

Suitable salt of the compound [II] may be acid addition salt as exemplified for the compound [I].

Suitable salts of the compound [III] may be base salt as exemplified for the compound [I].

Suitable salt of the compound [I-1] may be the same as those exemplified for the compound [I].

This reaction is preferably carried out in the presence of a base such as alkali metal [e.g. lithium, sodium, potassium, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], trialkylamine [e.g. trimethylamine, triethylamine, etc.], picoline, 1,5-diazabicyclo[4,3,0]non-5-ene, 1,4-diazabicyclo[2,2,2]octane, 1,8-diazabicyclo[5,4,0]undec-7-ene, or the like.

The reaction is usually carried out in a conventional solvent such as dioxane, tetrahydrofuran, pyridine or any other organic solvent which does not adversely influence the reaction.

The reaction temperature is not critical, and the reaction is usually carried out under cooling to heating.

Process 2

The compound [I-2] or its salt can be prepared by reacting a compound [IV] or its salt with a haloalkylating agent.

Suitable salts of the compounds [IV] and [I-2] may be acid addition salts as exemplified for the compound [I].

Suitable haloalkylating agent may be a metal salt of halo(lower)alkanoic acid [e.g. sodium trifluoroacetate, sodium pentafluoropropionate, etc.] and the like.

The present reaction is preferably carried out in the presence of a copper salt [e.g. cuprous iodide, etc.] and the like.

The reaction is usually carried out in a solvent N,N-dimethylacetamide, N,N-dimethylformamide or any other organic solvent which does not adversely influence the reaction.

The reaction temperature is not critical, and the reaction is usually carried out under warming or heating.

Process 3

The compound [I-3] or its salt can be prepared by reacting a compound [V] or its salt with an acylating agent.

Suitable salts of the compounds [V] and [I-3] may be acid addition salts as exemplified for the compound [I].

Suitable acylating agent may be a conventional one used in the Friedel-Crafts acylation reaction such as an acid halide [e.g. acid chloride, acid bromide, etc.], an acid anhydride or the like.

This reaction is preferably carried out in the presence of a Lewis acid such as aluminum halide [e.g. aluminum chloride, aluminum bromide, etc.], titanium halide [e.g. titanium tetrachloride, etc.] or the like.

The reaction is usually carried out in a conventional solvent such as carbon disulfide, dichloroethane, benzene or any other organic solvent which does not adversely influence the reaction.

The reaction temperature is not critical, and the reaction is usually carried out under cooling to heating.

Process 4

The compound [I-5] or its salt can be prepared by reacting a compound [I-4] or its salt with a compound [IV].

Suitable salts of the compounds [I-4] and [I-5] may be acid addition salts as exemplified for the compound [I].

The present reaction is preferably carried out in the presence of a thallium(III) salt [e.g. thallium(III) nitrate, etc.], an acid [e.g. perchloric acid, etc.] and the like.

The reaction is usually carried out in a solvent such as dioxane, tetrahydrofuran or any other organic solvent which does not adversely influence the reaction.

The reaction temperature is not critical and the reaction is preferably carried out at ambient temperature or under warming to heating.

Process 5

The compound [I-7] or its salt can be prepared by subjecting a compound [I-6] or its salt to deesterification reaction.

Suitable salt of the compound [I-6] may be acid addition salt as exemplified for the compound [I].

Suitable salt of the compound [I-7] may be the same as those exemplified for the compound [I].

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4,3,0]non-5-ene, 1,4-diazabicyclo[2,2,2]octane, 1,8-diazabicyclo[5,4,0]undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 6

The compound [I-9] or its salt can be prepared by reacting a compound [I-8] or its reactive derivative at the carboxy or sulfo group or a salt thereof with an amine, or formamide and alkali metal alkoxide.

Suitable salts of the compound [I-8] and its reactive derivative at the carboxy or sulfo group may be acid addition salts as exemplified for the compound [I].

Suitable "amine" may be ammonia, lower alkylamine, halo(lower)alkylamine, arylamine, lower alkylhydroxylamine, lower alkylamino(lower)alkylamine, amine substituted with a heterocyclic group, an amino acid ester, N-containing heterocyclic compound and the like.

The lower alkylamine may be mono or di(lower)alkylamine such as methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine, N-methylethylamine, N-methylpropylamine or the like, in which preferable one is methylamine, dimethylamine, ethylamine, diethylamine, isopropylamine, N-methylethylamine or N-methylpropylamine.

The halo(lower)alkylamine may be fluoromethylamine, chloroethylamine, difluoroethylamine, dichloroethylamine, trichloroethylamine, trifluoroethylamine and the like, in which preferable one is trifluoroethylamine.

The arylamine may be aniline, naphthylamine and the like, in which preferable one is aniline.

The lower alkylhydroxylamine may be methylhydroxylamine, ethylhydroxylamine, propylhydroxylamine, butylhydroxylamine, isopropylhydroxylamine and the like, in which preferable one is methylhydroxylamine.

The lower alkylamino(lower)alkylamine may be dimethylaminomethylamine, diethylaminomethylamine, dimethylaminoethylamine, diethylaminoethylamine and the like, in which preferable one is dimethylaminoethylamine.

The amine substituted with a heterocyclic group may be aminothiazole, aminothiadiazole, aminotriazole, aminotetrazole and the like, in which preferable one is aminotetrazole.

The amino acid ester may be amino acid lower alkyl ester [e.g. glycine methyl ester, N-methylglycine ethyl ester, β-alanine methyl ester, isoleucine ethyl ester, etc.], amino acid ar(lower)alkyl ester [e.g. glycine benzyl ester,N-methylglycine benzyl ester, β-alanine benzyl ester, etc.] and the like, in which preferable one is N-methylglycine ethyl ester.

The N-containing heterocyclic compound may be saturated 5 or 6-membered N-, or N- and S-, or N- and O-containing heterocyclic compound such as pyrrolidine, imidazolidine, piperidine, piperazine, N-(lower)alkylpiperazine [e.g. N-methylpiperazine, N-ethylpiperazine, etc.],morpholine, thiomorpholine or the like, in which preferable one is morpholine, N-methylpiperazine or pyrrolidine.

Suitable "alkali metal alkoxide" may be sodium methoxide, sodium ethoxide, potassium tert-butoxide and the like.

Suitable reactive derivative at the carboxy or sulfo group of the compound [I-8] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with 1,1'-carbonyl diimidazole or an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound [I-8] is used in a free acid form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like. The reaction is also preferably carried out in the presence of a conventional base such as triethylamine, pyridine, sodium hydroxide or the like.

The reaction temperature is not critical, and the reaction can be carried out under cooling to heating.

Process 7

The compound [I-11] or its salt can be prepared by reacting a compound [I-10] or its salt with a compound [VII].

Suitable salt of the compound [I-10] may be acid addition salt as exemplified for the compound [I].

Suitable salt of the compound [I-11] may be the same as those exemplified for the compound [I].

This reaction is preferably carried out in the presence of a base such as alkali metal [e.g. lithium, sodium, potassium, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] or the like.

The reaction is usually carried out in a conventional solvent such as an alcohol [e.g. methanol, ethanol, etc.], dioxane, tetrahydrofuran, N,N-dimethylformamide or any other organic solvent which does not adversely influence the reaction.

The reaction temperature is not critical, and the reaction is usually carried out under cooling to heating.

Process 8

The compound [I-13] or its salt can be prepared by reacting a compound [I-12] or its salt with an oxidizing agent.

Suitable salts of the compounds [I-12] and [I-13] may be the same as those exemplified for the compound [I].

Suitable oxidizing agent may be hydrogen peroxide, Jones reagent, peracid [e.g. peracetic acid, perbenzoic acid, m-chloroperbenzoic acid, etc.], chromic acid, potassium permanganate, alkali metal periodate [e.g. sodium periodate, etc.] and the like.

This reaction is usually carried out in a solvent which does not adversely influence the reaction such as acetic acid, dichloromethane, acetone, ethyl acetate, chloroform, water, an alcohol [e.g. methanol, ethanol, etc.], a mixture thereof or the like.

The reaction temperature is not critical, and the reaction is usually carried out under cooling to warming.

In this reaction, in case that the compound [I-12] having acylamino(lower)alkyl or lower alkyl(acyl)amino(lower)alkyl for $R^1$ is used as a starting compound, the compound [I-13] having amino(lower)alkyl or lower alkylamino(lower)alkyl for $R^1$ may be obtained respectively according to reaction conditions. These cases are included within the scope of the present reaction.

Process 9

The compound [I-15] or its salt can be prepared by reacting a compound [I-14] or its salt with an oxidizing agent.

Suitable salts of the compounds [I-14] and [I-15] may be the same as those exemplified for the compound [I].

Suitable oxidizing agent may be the same as those exemplified in Process 8.

This reaction can be carried out in substantially the same manner as Process 8, and therefore the reaction mode and reaction condition [e.g. solvent, reaction temperature, etc.] of this reaction are to be referred to those as explained in Process 8.

Process 10

The compound [I-16] or its salt can be prepared by reacting a compound [I-3] or its salt with an oxidizing agent.

Suitable salts of the compounds [I-3] and [I-16] may be the same as those exemplified for the compound [I].

Suitable oxidizing agent may be the same as those exemplified in Process 8.

This reaction can be carried out in substantially the same manner as Process 8, and therefore the reaction mode and reaction condition [e.g. solvent, reaction temperature, etc.] of this reaction are to be referred to those as explained in Process 8.

Process 11

The compound [I-18] or its salt can be prepared by reacting a compound [I-17] or its salt with a reducing agent.

Suitable salts of the compounds[I-17] and [I-18] may be the same as those exemplified for the compound [I].

Suitable reducing agent may be aluminum hydride compound [e.g. lithium aluminum hydride, lithium tri-t-butoxy-aluminum hydride, etc.], borohydride compound [e.g. sodium borohydride, etc.], aluminum alkoxide [e.g. aluminum isopropoxide, etc.] and the like.

The reaction is usually carried out in a conventional solvent, such as water, an alcohol [e.g. methanol, ethanol, propanol, isopropanol, etc.], chloroform, diethyl ether, dioxane, or any other organic solvent which does not adversely influence the reaction, or a mixture thereof.

The reaction temperature is not critical, and the reaction can be carried out under cooling to heating.

Process 12

The compound [I-19] or its salt can be prepared by reacting a compound [I-3] or its salt with a compound [VIII] or its salt.

Suitable salts of the compounds [I-3], [I-19] and [VIII] may be acid addition salts as exemplified for the compound [I].

The reaction is usually carried out in a conventional solvent such as water, an alcohol [e.g. methanol, ethanol, etc.], acetone, dioxane, acetonitrile, chloroform, methylene chloride, ethylene chloride, tetrahydrofuran, ethyl acetate, N,N-dimethylformamide, dioxane or any other organic solvent which does not adversely influence the reaction. These conventional solvents may also be used in a mixture with water.

The reaction is preferably carried out in the presence of an inorganic or organic base such as alkali metal bicarbonate [e.g. sodium bicarbonate, potassium bicarbonate, etc.], alkali metal carbonate [e.g. sodium carbonate, potassium carbonate, etc.], tri(lower)alkylamine [e.g. triethylamine, etc.], pyridine, or the like.

The reaction temperature is not critical, and the reaction is usually carried out under cooling to heating.

Process 13

The compound [I-20] or its salt can be prepared by reacting a compound [V] or its salt with a nitrating agent or a sulfonating agent.

Suitable salts of the compounds [I-20] and [V] may be acid addition salts as exemplified for the compound [I].

Suitable nitrating agent may be nitric acid, fuming nitric acid, potassium nitrate, nitronium tetrafluoroborate and the like.

Suitable sulfonating agent may be sulfuric acid, fuming sulfuric acid and the like.

The reaction is usually carried out in an acid or an acid anhydride such as sulfuric acid, acetic acid, acetic anhydride or the like.

The reaction temperature is not critical, and the reaction is usually carried out under cooling to heating.

Process 14

The compound [I-22] or its salt can be prepared by subjecting a compound [I-21] or its salt to reduction.

Suitable salts of the compounds [I-21] and [I-22] may be acid addition salts as exemplified for the compound [I].

The present reduction is carried out by chemical reduction, catalytic reduction, or the like.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming.

In this reaction, in case that the compound [I-21] having aryl substituted with nitro for $R^2$ and/or aryl substituted with nitro for $R^3$ is used as a starting compound, the compound [I-22] having aryl substituted with amino for $R^2$ and/or aryl substituted with amino for $R^3$ may be obtained according to reaction conditions. This case is included within the scope of the present reaction.

Process 15

The compound [I-24] or its salt can be prepared by subjecting a compound [I-23] or its salt to reduction.

Suitable salts of the compounds [I-23] and [I-24] may be the same as those exemplified for the compound [I].

This reaction can be carried out in substantially the same manner as Process 14, and therefore the reducing agent, the reaction mode and the reaction condition [e.g. solvent, reaction temperature, etc.] of this reaction are to be referred to those as explained in Process 14.

In this reaction, in case that the compound [I-23] having nitro for $R^1$ and/or aryl substituted with nitro for $R^3$ is used as a starting compound, the compound [I-24] having amino for $R^1$ and/or aryl substituted with amino for $R^3$ may be obtained according to reaction conditions. This case is included within the scope of the present reaction.

Process 16

The compound [I-26] can be prepared by reacting a compound [I-25] or its salt with an acylating or sulfonylating agent.

Suitable salt of the compound [I-25] may be acid addition salt as exemplified for the compound [I].

The acylating or sulfonylating agent may include an organic acid represented by the formula: $R^8$—OH, in which $R^8$ is acyl or lower alkylsulfonyl as illustrated above, or a reactive derivative thereof, a compound of the formula: R⁴—N=C=O, wherein R⁴ is as defined above, and the like.

Suitable reactive derivative of the organic acid may be a conventional one such as an acid halide [e.g. acid chloride, acid bromide, etc.], an acid azide, an acid anhydride, an activated amide, an activated ester, etc.

When free acid is used as an acylating or sulfonylating agent, the present reaction may preferably be carried out in the presence of conventional condensing agent such as N,N'-dicyclohexylcarbodiimide, acetic anhydride or the like.

This reaction is usually carried out in a conventional solvent such as dioxane, chloroform, methylene chloride, tetrahydrofuran, pyridine or any other organic solvent which does not adversely influence the reaction.

The reaction may also be carried out in the presence of an inorganic or organic base such as an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. triethylamine, etc.], or the like.

The reaction temperature is not critical, and the reaction can be carried out under cooling to heating.

In this reaction, in case that the compound [I-25] having aryl substituted with amino for $R^3$ is used a starting compound, the compound [I-26] having aryl substituted with acylamino or lower alkylsulfonylamino for $R^3$ may be obtained according to reaction conditions. This case is included within the scope of the present reaction.

Process 17

The compound [I-28] can be prepared by reacting a compound [I-27] or its salt with a sulfonylating agent.

Suitable salt of the compound [I-27] may be acid addition salt as exemplified for the compound [I].

This reaction can be carried out in substantially the same manner as Process 16, and therefore the sulfonylating agent, the reaction mode and the reaction condition [e.g. solvent, reaction temperature, etc.] of this reaction are to be referred to those as explained in Process 16.

In this reaction, in case that the compound [I-27] having aryl substituted with amino for $R^3$ is used as a starting compound, the compound [I-28] having aryl substituted with lower alkylsulfonylamino for $R^3$ may be obtained according to reaction conditions. This case is included within the scope of the present reaction.

Process 18

The compound [I-30] or its salt can be prepared by reacting a compound [I-29] or its salt with a reducing agent.

Suitable salts of the compounds [I-29] and [I-30] may be acid addition salts as exemplified for the compound [I].

Suitable reducing agent may be diborane, a metal hydride [e.g. lithium aluminum hydride, etc.] and the like.

The reaction is usually carried out in a conventional solvent such as diethyl ether, tetrahydrofuran or any other organic solvent which does not adversely influence the reaction.

The reaction temperature is not critical, and the reaction can be carried out under cooling to heating.

Process 19

The compound [I-31] or its salt can be prepared by reacting a compound [V] or its salt with a formylating agent.

Suitable salts of the compounds [V] and [I-31] may be acid addition salts as exemplified for the compound [I].

Suitable formylating agent may be N,N-dimethylformamide; so-called Vilsmeir reagent prepared by the reaction of N,N-dimethylformamide with phosphorus oxychloride, phosgene, etc.; and the like.

When a formylating agent is N,N-dimethylformamide, the reaction is preferably carried out in the presence of a base such as lower alkyl alkali metal [e.g. n-butyl lithium, etc.], or the like.

The reaction is usually carried out in a solvent such as dioxane, tetrahydrofuran, N,N-dimethylformamide, methylene chloride, chloroform, or any other organic solvent which does not adversely influence the reaction.

The reaction temperature is not critical, and the reaction is usually carried out under cooling to heating.

Process 20

The compound [I-32] can be prepared by the following methods. Namely, 1) the compound [Va] is firstly reacted with a chlorosulfonylating agent, and then 2) reacting the resultant product with an amine.

Suitable "amine" may be the same as those exemplified in Process 6.

In the first step, suitable chlorosulfonylating agent may be chlorosulfonic acid, and the like. In this reaction, the chlorosulfonylating agent is usually used as a solvent. The reaction temperature is not critical, and the reaction is usually carried out under cooling to heating.

In the second step, the reaction is carried out in a solvent such as water, ethyl acetate, tetrahydrofuran or any other solvent which does not adversely influence the reaction. This reaction temperature is not critical, and the reaction is usually carried out under cooling.

Process 21

The compound [I-34] or its salt can be prepared by reacting a compound [I-33] or its salt with thiourea or lower(alkyl)thiourea.

Suitable salts of the compounds [I-33] and [I-34] may be acid addition salts as exemplified for the compound [I].

The reaction is usually carried out in a solvent such as an alcohol [e.g. methanol ethanol, etc.], chloroform, methylene chloride, tetrahydrofuran, dioxane or any other organic solvent which does not adversely influence the reaction.

The reaction temperature is not critical, and the reaction can be carried out under cooling to heating.

Process 22

The compound [I-36] or its salt can be prepared by reacting a compound [I-35] or its salt with a compound [IX].

Suitable salts of the compounds [I-35] and [I-36] may be acid addition salts as exemplified for the compound [I].

This reaction is preferably carried out in the presence of an inorganic or organic base such as an alkali metal [e.g. sodium, potassium, etc.], an alkaline earth metal [e.g. magnesium, calcium, etc.], the hydroxide or carbonate thereof, alkali metal hydride [e.g. sodium hydride, etc.], alkali metal amide [e.g. sodium amide, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], lower alkyl alkali metal [e.g. n-butyl lithium, etc.], trialkylamine [e.g. trimethylamine, triethylamine, etc.], pyridine, piperidine, picoline, 1,5-diazabicyclo[4,3,0]non-5-ene, 1,4-diazabicyclo[2,2,0]octane, 1,8-diazabicyclo[5,4,0]undec-7-ene, or the like.

The reaction is usually carried out in a solvent such as water, an alcohol [e.g. methanol, ethanol, etc.], chloroform, methylene chloride, nitromethane, benzene, tetrahydrofuran, diethyl ether, N,N-dimethylformamide, dimethylsulfoxide or any other organic solvent which does not adversely influence the reaction.

The reaction temperature is not critical, and the reaction can be carried out under cooling to heating.

In this reaction, in case that the corresponding phosphorane compound derived from the compound [IX] is stable, the phosphorane compound may be used instead of the compound [IX]. This case is also included within the scope of the present reaction.

Process 23

The compound [I-38] or its salt can be prepared by subjecting a compound [I-37] or its salt to reduction.

Suitable salts of the compounds [I-37] and [I-38] may be the same as those exemplified for the compound [I].

This reaction can be carried out in substantially the same manner as Process 14, and therefore the reducing agent, the reaction mode and the reaction condition [e.g. solvent, reaction temperature, etc.] of this reaction are to be referred to those as explained in Process 14.

In this reaction, in case that the compound [I-37] having nitro for $R^1$ and/or aryl substituted with nitro for $R^2$ is used as a starting compound, the compound [I-38] having amino for $R^1$ and/or aryl substituted with amino for $R^2$ may be obtained according to reaction conditions. This case is included within the scope of the present reaction.

Process 24

The compound [I-40] can be prepared by reacting a compound [I-39] or its salt with an acylating agent.

Suitable salt of the compound [I-39] may be acid addition salt as exemplified for the compound [I].

This reaction can be carried out in substantially the same manner as Process 16, and therefore the acylating agent, the reaction mode and the reaction condition [e.g. solvent, reaction temperature, etc.] of this reaction are to be referred to those as explained in Process 16.

Process 25

The compound [I-41] can be prepared by reacting a compound [I-40] with an alkylating agent.

Suitable alkylating agent may be lower alkyl halide [e.g. methyl iodide, ethyl bromide, etc.] and the like.

When lower alkyl halide is used as alkylating agent, the reaction is preferably carried out in the presence of a base such as an alkali metal [e.g. sodium, potassium, etc.], an alkaline earth metal [e.g. magnesium, calcium, etc.], the hydride thereof or the like.

The reaction is usually carried out in a conventional solvent which does not adversely influence the reaction such as dioxane, tetrahydrofuran, N,N-dimethylformamide, or a mixture thereof. Additionally, in case that the above-mentioned alkylating agent are in liquid, they can also be used as a solvent.

The reaction temperature is not critical and the reaction can be carried out under cooling to heating.

Process 26

The compound [I-43] or its salt can be prepared by reacting a compound [I-42] or its salt with a dehydrating agent.

Suitable salts of the compounds [I-42] and [I-43] may be acid addition salts as exemplified for the compound [I].

Suitable dehydrating agent may be phosphorus compound [e.g. phosphorus pentoxide, phosphorus pentachloride, phosphorus oxychloride, etc.], thionyl chloride, acid anhydride [e.g. acetic anhydride, etc.], phosgene, arylsulfonyl chloride [e.g. benzenesulfonyl chloride, p-toluenesulfonyl chloride, etc.], methanesulfonyl chloride, sulfamic acid, ammonium sulfamate, N,N'-dicyclohexylcarbodiimide, lower alkoxycarbonyl halide [e.g. ethyl chloroformate, etc.] and the like.

The reaction is usually carried out in a conventional solvent such as acetonitrile, methylene chloride, ethylene chloride, benzene, N,N-dimethylformamide, pyridine or any other organic solvent which does not adversely influence the reaction.

Additionally in case that the above-mentioned dehydrating agents are in liquid, they can also be used as a solvent.

The reaction temperature is not critical and the reaction is preferably carried out under warming or heating.

Process 27

The compound [I-44] or its salt can be prepared by subjecting a compound [I-41] to deacylation reaction.

Suitable salt of the compound [I-44] may be acid addition salt as exemplified for the compound [I].

This reaction may preferably be conducted in the presence of an inorganic acid [e.g. hydrochloric acid, hydrobromic acid, etc.] and an organic acid [e.g. trifluoroacetic acid, methanesulfonic acid, toluenesulfonic acid, etc.].

The reaction is usually carried out in a conventional solvent such as water, an alcohol [e.g. methanol, ethanol, etc.], tetrahydrofuran, dioxane or any other organic solvent which does not adversely influence the reaction, or a mixture thereof.

The reaction temperature is not critical, and the reaction can be carried out cooling to heating.

Process 28

The compound [I-45] or its salt can be prepared by reacting a compound [I-43] or its salt with an azide compound.

Suitable salts of the compounds [I-43] and [I-45] may be the same as those exemplified for the compound [I].

Suitable azide compound may be alkali metal azide [e.g. sodium azide, potassium azide, etc.], alkaline earth metal azide [e.g. calcium azide, etc.], hydrogen azide and the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out warming to heating.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compound [I] and pharmaceutically acceptable salts thereof possess strong antiinflammatory and analgesic activities, and are useful for the treatment and/or prevention of inflammatory conditions and various pains, collagen diseases, autoimmune diseases and various immunity diseases in human beings or animals, and more particularly to methods for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition [e.g. conjunctivitis, etc.], lung disorder in which inflammation is involved [e.g. asthma, bronchitis, pigeon fancier's disease, farmer's lung, etc.], condition of the gastrointensinal tract associated with inflammation [e.g. aphthous ulcer, Chrohn's disease, atropic gastritis, gastritis varialoforme, ulcerative colitis, coeliac disease, regional ileitis, irritable bowel syndrome, etc.], gingivitis, inflammation, pain and tumescence after operation or injury, pyresis, pain and other conditions associated with inflammation, particularly those in which lipoxygenase and cyclooxygenase products are a factor, systemic lups erythematosus, scleroderma, polymyositis, periarteritis nodosa, rheumatic fever, Sjögren's syndrome, Behcet disease, thyroiditis, type I diabetes, nephrotic syndrome, aplastic anemia, myasthenia gravis, uveitis contact dermatitis, psoriasis, Kawasaki disease, sarcoidosis, Hodgkin's disease, and the like.

In order to illustrate the usefulness of the object compound [I], the pharmacological test data of the compound [I] are shown in the following.

[A] ANTIINFLAMMATORY ACTIVITY

Effect on adjuvant arthritis in rats:
(i) Test Method:
Ten female Sprague-Dawley rats were used per group. A dose of 0.5 mg of Mycobacterium tuberculosis (strain Aoyama B) suspended in 0.05 ml of liquid paraffin was injected subcutaneously in the right hind paw. The injection of mycobacterial adjuvant produced local inflammatory lesions (primary lesion) and then about 10 days later, secondary lesions in both the injected and uninjected paws. The difference in volumes of both paws before and after adjuvant injection was the measure of arthritis. The drug was given orally once a day for 23 consecutive days from day 1.
(ii) Test Results:

| Test compound (Example No.) | Dose (mg/kg) | Inhibition of secondary lesion (uninjected paw) (%) |
| --- | --- | --- |
| 4 | 0.1 | 87.0 |
| 5-2) | 10 | 97.4 |
| 28 | 10 | 95.6 |
| 35 | 3.2 | 87.1 |
| 47-3) | 10 | 96.9 |
| 53 | 10 | 88.8 |
| Ibuprofen | 100 | 79.6 |

[B] ANALGESIC ACTIVITY

Inflammatory hyperalgesia induced by brewer's yeast in rats:
(i) Test Method:
Ten male Sprague Dawley rats were used per group. 0.1 ml of 5% brewer's yeast suspended in 0.5% methylcellulose was injected into the right hind paw. The pain threshold was determined 3 hours after yeast injection, by applying pressure to the foot and reading the pressure at which the rat withdrew the foot.

The drugs were given orally 2 hours after yeast injection. The pain threshold in the treated animals was compared with that in the control animals.
(ii) Test Results:

| Test compound (Example No.) | Dose (mg/kg) | Relative potency (Control = 1.0) |
| --- | --- | --- |
| 6 | 32 | 1.41 |
| 15-24) | 32 | 1.41 |
| 18-8) | 32 | 1.32 |
| 22-17) | 32 | 1.35 |
| 46-2) | 32 | 1.41 |
| 62-5) | 10 | 1.50 |
| 70-3) | 10 | 1.32 |

[C] ANTI-RHEUMATIC ACTIVITY

Effect on collagen induced arthritis in mice:
(i) Test Method:

Eight male DBA/1 mice were used per group. Type II bovine collagen was solublized in 0.1M acetic acid and emulsified in complete Freund's adjuvant (CFA). Mice were primed with 0.2 mg of Type II collagen in CFA intradermally at the base of the tail. Mice were challenged after 21 day with the same procedure. From 10 day after challenge, drug was administered orally once a day for 3 weeks and mice were inspected weekly for visual signs of arthritis. An arthritis index was used to grade limb 0–3, representing joint swelling and erythema (Grade 1), visible joint disorder (Grade 2) and detectable joint ankylosis (Grade 3).
(ii) Test Results:

| Test compound (Example No.) | Dose (mg/kg) | Inhibition of arthritis index (%) |
| --- | --- | --- |
| 4) | 0.1 | 56.3 |
| 5-2) | 10 | 66.7 |
| 53 | 10 | 54.8 |

[D] Effect on Delayed Type Hypersensitivity (DTH)

Response to bovine type II collagen
(i) Test Method:
Seven male DBA/1 mice were used for this test. The mice were sensitized at tail base with 125 μg type II collagen emulsified in complete Freund's adjuvant containing Mycobacterium tuberculosis strain H37Rv (Wako Pure Chemical Industries Ltd., Osaka, Japan). Two weeks' later, a 0.04 ml challenge dose of 2.5 mg/ml type II collagen in phosphate buffered saline (PBS) was injected into the plantar region of the right hind foot and 0.04 ml PBS into the left hind foot to act as a control. Twenty four hours after challenge, the volume of both hind feet were measured with a volume meter (Muromachi MK-550).

The drug was administered orally on consecutive days except holidays starting from the sensitization.

Data was expressed by per cent inhibition compared with vehicle control for each study.
(ii) Test Results:

| Test Compound (Example No.) | Dose (mg/kg) | |
| --- | --- | --- |
|  | 1.0 | 10 |
| 4 | 67.7 | 79.0 |

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external (topical) administration. The pharmaceutical preparations may be capsules, tablets, dragees, granules, suppositories, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

A mixture of phosphorus oxychloride (1.6 ml) and N,N-dimethylformamide (1.8 ml) in dichloroethane (6 ml) was stirred at ambient temperature for 1 hour. Dichloroethane (11 ml) and 4'-fluoro-2-(4-nitrophenyl)acetophenone (3 g) was added, and the mixture was refluxed overnight, washed with water twice, dried and evaporated. The oily residue (4 g) was purified by column chromatography on silica gel (80 g) eluting with toluene to give yellow crystals of 3-chloro-3-(4-fluorophenyl)-2-(4-nitrophenyl)propenal (2.9 g).

IR (Nujol): 1680, 1600, 1520 cm$^{-1}$
NMR (CDCl$_3$, δ): 6.8–8.4 (8H, m), 9.64 (1H, s)

Preparation 2

A mixture of 3,4-difluorophenylacetic acid (10 g), 4-(methylthio)benzaldehyde (8.84 g) and sodium methoxide (3.14 g) in acetic anhydride (30 ml) was refluxed for 20 hours. The solvent was evaporated, and the residue was dissolved in ethyl acetate, washed with dilute hydrochloric acid and water, dried and concentrated to dryness. The obtained solid material was washed with ethanol and dried to give crystals of 2-(3,4-difluorophenyl)-3-[4-(methylthio)phenyl]acrylic acid (12.1 g).

mp: 154°–158° C.
IR (Nujol): 1665, 1585, 1515 cm$^{-1}$
NMR (DMSO-d$_6$, δ): 2.07 (3H, s), 6.6–7.4 (7H, m), 7.40 (1H, s), 12.4 (1H, s)
Mass (m/z): 306 (M$^+$), 262

Preparation 3

A mixture of 2-(3,4-difluorophenyl)-3-[4-(methylthio)phenyl]acrylic acid (12 g) and phosphorus pentachloride (9.0 g) in dichloromethane (120 ml) was stirred for 1 hour. The solvent was evaporated to give a solid of 2-(3,4-difluorophenyl)-3-[4-(methylthio)phenyl]acryloyl chloride (13 g).

IR (Nujol): 1740, 1615, 1585, 1515 cm$^{-1}$

A solution of the above acid chloride (13 g) in acetone (50 ml) was added dropwise to an ice-cooled mixture of sodium azide (2.8 g) and sodium bicarbonate (8.2 g) in water (50 ml) and acetone (50 ml). The mixture was stirred for 1 hour at ambient temperature, and acetone was evaporated. The resulting aqueous solution was extracted with toluene. The extract was washed with water, dried and concentrated to give a solid of 2-(3,4-difluorophenyl)-3-[4-(methylthio)phenyl]acryloyl azide.

IR (Nujol): 2150, 1680, 1590, 1510 cm$^{-1}$

A mixture of the above acid azide, water (25 ml) and acetic acid (50 ml) was refluxed for 1 hour, and cooled overnight. The precipitates were collected and recrystallized from ethanol to give crystals of 3',4'-difluoro-2-[4-(methylthio)phenyl]acetophenone (8.3 g).

mp: 123°–124° C.
IR (Nujol): 1690, 1610, 1515 cm$^{-1}$
NMR (CDCl$_3$, δ): 2.46 (3H, s), 4.19 (2H, s), 7.1–7.9 (7H, m)
Mass (m/z): 278

The following compound (Preparation 4) was obtained according to a similar manner to that of Preparation 3.

Preparation 4

4'-Nitro-2-[4-(methylthio)phenyl]acetophenone
mp: 105°–107° C.
IR (Nujol): 1695, 1600, 1520 cm$^{-1}$
NMR (CDCl$_3$, δ): 2.47 (3H, s), 4.28 (2H, s), 7.1–7.3 (4H, m), 8.13 (2H, d, J=8 Hz), 8.27 (2H, d, J=8 Hz)
Mass (m/z): 287 (M$^+$)

Preparation 5

A mixture of 5-(4-fluorophenyl)-4-(4-nitrophenyl)thiophene-2-carboxylic acid (7.6 g) and copper powder (1.6 g) in quinoline (12 ml) was stirred and refluxed for 7 hours. The reaction mixture was diluted with ethyl acetate and filtered. The filtrate was washed with water, brine, dilute hydrochloric acid and brine, successively, dried and evaporated. The residue (7.3 g) was purified by column chromatography on silica gel (80 g) eluting with a mixture of hexane and toluene (2:1) to give yellow orange crystals of 2-(4-fluorophenyl)-3-(4-nitrophenyl)thiophene (3.8 g).

mp: 108°–110° C.
IR (Nujol): 1600, 1540, 1510 cm$^{-1}$

The following compounds (Preparation 6-1) to 6-6)) were obtained according to a similar manner to that of Preparation 5.

Preparation 6

1) 2-(4-Fluorophenyl)-3-(4-methoxyphenyl)thiophene
IR (Nujol): 1605, 1545, 1510, 1500 cm$^{-1}$ 2) 2-(4-Chlorophenyl)-3-[4-(methylthio)phenyl]thiophene
mp: 133°14 134° C.
IR (Nujol): 1600, 1490 cm$^{-1}$ 3) 3-[4-(Ethylthio)phenyl]-2-(4-fluorophenyl)thiophene
IR (Film): 1605, 1535, 1505 cm$^{-1}$
NMR (CDCl$_3$, δ): 1.31 (3H, t, J=7 Hz), 2.92 (2H, q, J=7 Hz), 6.7–7.4 (10H, m)

4) 2-(3,4-Difluorophenyl)-3-[4-(methylthio)phenyl]thiophene
mp: 94°–96° C.
IR (Nujol): 1600, 1515 cm$^{-1}$
Mass (m/z): 318 (M$^+$)

5) 3-[4-(Methylsulfonyl)phenyl]-2-(4-nitrophenyl)thiophene
mp: 145°–150° C. (dec.)
IR (Nujol): 1595, 1510 cm$^{-1}$
NMR (DMSO-d$_6$, δ): 3.25 (3H, s), 7.39 (1H, d, J=5 Hz), 7.4–8.0 (7H, m), 8.21 (2H, d, J=8 Hz)
Mass (m/z): 359 (M$^+$)

6) 3-[4-(Methylthio)phenyl]-2-(4-nitrophenyl)thiophene
mp: 135°–140° C.
NMR (DMSO-d$_6$, δ): 2.47 (3H, s), 6.8–8.2 (10H, m)

Preparation 7

Bromine (1 ml) was added dropwise to a solution of 2-(4-fluorophenyl)-3-(4-nitrophenyl)thiophene (5.3 g) in acetic acid (53 ml) and dichloromethane (53 ml) at 2° C. The mixture was stirred at 2° C. for 45 minutes and concentrated to dryness. The residue was collected and washed with water and ethanol to give dark green crystals of 5-bromo-2-(4-fluorophenyl)-3-(4-nitrophenyl)thiophene (6.5 g).

mp: 129°–130° C.
IR (Nujol): 1605, 1595, 1545, 1510 cm$^{-1}$
NMR (DMSO-d$_6$, δ): 7.1–7.6 (7H, m), 8.17 (2H, d, J=9 Hz)
Mass (m/z): 378 (M$^+$)

The following compounds (Preparations 8-1) and 8-2)) were obtained according to a similar manner to that of Preparation 7.

Preparation 8

1) 5-Bromo-3-[4-(methylsulfonyl)phenyl]-2-(4-nitrophenyl)thiophene
mp: 178°–180° C. (dec.)
IR (Nujol): 1595, 1515 cm$^{-1}$
NMR (DMSO-d$_6$, δ): 3.25 (3H, s), 7.4–7.6 (5H, m), 7.90 (2H, d, J=8 Hz), 8.20 (2H, d, J=8 Hz)
Mass (m/z): 439, 437

2) 5-Bromo-3-[4-(methylthio)phenyl]-2-(4-nitrophenyl)thiophene
mp: 230° C. (dec.)
IR (Nujol): 1600, 1515 cm$^{-1}$
Mass (m/z): 407, 405

The following compound (Preparation 9) was obtained according to a similar manner to that of preparation 2.

Preparation 9

2-(4-Nitrophenyl)-3-[4-(methylthio)phenyl]acrylic acid
mp: 217°–219° C. (dec.)

IR (Nujol): 1690, 1670, 1610, 1590, 1515 cm$^{-1}$

NMR (DMSO-d$_6$, δ): 2.42 (3H, s), 6.98 (2H, d, J=8 Hz), 7.10 (2H, d, J=8 Hz), 7.42 (2H, d, J=8 Hz), 7.83 (1H, s), 8.25 (2H, d, J=8 Hz), 12.8 (1H, s)

Mass (m/z): 315 (M$^+$)

Preparation 10

A mixture of 3-[4-(methylthio)phenyl]-2-(4-nitrophenyl)thiophene (0.33 g) and N-chlorosuccinimide (0.15 g) in acetic acid (5 ml) was heated at 80° C. for 3 hours. The mixture was poured into an ice-cooled solution of sodium bicarbonate, and the precipitates were collected to give a powder of 5-chloro-3-[4-(methylthio)phenyl]-2(4-nitrophenyl)thiophene (0.31 g).

mp: 150°–160° C. (dec.)

IR (Nujol): 1595, 1515 cm$^{-1}$

NMR (CDCl$_3$, δ): 2.49 (3H, s), 6.9–8.2 (9H, m)

Preparation 11

A mixture of 5-(4-fluorophenyl)-4-[4-(methylsulfonyl)phenyl]thiophene-2-carboxamide (4.8 g) and methanesulfonyl chloride (8.8 g) in pyridine (25 ml) was stirred at 50° C. for 4 hours. The mixture was concentrated and the residue was triturated in dilute hydrochloric acid. The precipitates were collected and recrystallized from ethanol to give crystals of 5-(4-fluorophenyl)-4-[4-(methylsulfonyl)phenyl]thiophene-2-carbonitrile (3.6 g).

mp: 139°–140° C.

IR (Nujol): 2220, 1600, 1510 cm$^{-1}$

NMR (DMSO-d$_6$, δ): 3.24 (3H, s), 7.1–7.6 (6H, m), 7.91 (2H, d, J=8 Hz), 8.24 (1H, s)

MASS (m/z): 357 (M$^+$)

EXAMPLE 1

A mixture of 3-chloro-3-(4-fluorophenyl)-2-(4-nitrophenyl)propenal (1.5 g), thioglycolic acid (0.36 ml) and triethylamine (1.5 ml) in pyridine (7.6 ml) was stirred at 70° C. for 1 hour and refluxed for 7 hours. Pyridine was evaporated, and the residue was dissolved in ethyl acetate, washed with water and dilute hydrochloric acid, dried and concentrated. The residue (1.6 g) was washed with toluene to give pale brown crystals of 5-(4-fluorophenyl)-4-(4-nitrophenyl)thiophene-2-carboxylic acid (1.1 g).

mp: 227°–229° C.

IR (Nujol): 1670, 1600, 1545, 1510 cm$^{-1}$

NMR (DMSO-d$_6$, δ): 7.2–7.6 (6H, m), 7.91 (1H, s), 8.18 (2H, d, J=9 Hz), 13.4 (1H, s)

Mass (m/z): 342, 299

EXAMPLE 2

A mixture of phosphorus oxychloride (3.2 ml) and N,N-dimethylformamide (3.4 ml) in dichloroethane (25 ml) was stirred at ambient temperature for 1 hour and 2',4'-difluoro-2-[4-(methylthio)phenyl]acetophenone (6.2 g) was added thereto. The mixture was refluxed for 8 hours, washed with water twice, dried and evaporated to give 3-chloro-3-(2,4-difluorophenyl)-2-[4(methylthio)phenyl]propenal as a solid.

A mixture of the above solid, ethyl thioglycolate (3 g) and triethylamine (5 g) in pyridine (35 ml) was stirred and refluxed for 6 hours. Solvent was evaporated, and the residue was dissolved in ethyl acetate, washed with water and dilute hydrochloric acid, dried and concentrated to give an oil of ethyl 5-(2,4-difluorophenyl)-4-[4-(methylthio)phenyl]thiophene-2-carboxylate (9 g).

IR (Film): 1710, 1600, 1545, 1495 cm$^{-1}$

NMR (CDCl$_3$, δ): 1.39 (3H, t, J=8 Hz), 2.41 (3H, s), 4.33 (2H, q, J=8 Hz), 6.3–7.9 (8H, m)

The following compounds (Examples 3-1) and 3-2)) were obtained according to a similar manner to that of Example 2.

EXAMPLE 3

1) Ethyl 5-(3,4-difluorophenyl)-4-[4-(methylthio)phenyl]thiophene-2-carboxylate

IR (Film): 1710, 1600, 1540, 1515 cm$^{-1}$

NMR (CDCl$_3$, δ): 1.38 (3H, t, J=7 Hz), 2.44 (3H, s), 4.33 (2H, q, J=7 Hz), 6.9–7.3 (7H, m), 7.69 (1H, s)

2) Ethyl 4-[4-(methylthio)phenyl]-5-(4-nitrophenyl)thiophene-2-carboxylate

IR (Film): 1710, 1600, 1520 cm$^{-1}$

NMR (CDCl$_3$, δ): 1.30 (3H, t, J=7 Hz), 2.48 (3H, s), 4.20 (2H, q, J=7 Hz), 7.1–7.3 (4H, m), 7.47 (2H, d, J=8 Hz), 7.82 (1H, s), 8.18 (2H, d, J=8 Hz)

Mass (m/z): 399 (M$^+$)

EXAMPLE 4

A mixture of 5-bromo-2-(4-fluorophenyl)-3-[4(methylsulfonyl)phenyl]thiophene (7.2 g), sodium trifluoroacetate (9.4 g) and cuprous iodide (6.5 g) in N,N-dimethylacetamide (109 ml), was stirred and refluxed for 5 hours. Dichloromethane (200 ml), 3N hydrochloric acid (100 ml) and water (100 ml) were added to the reaction mixture. The resulting mixture was filtered, and the filtrate was separated. The organic layer was washed with water, dried over magnesium sulfate and concentrated. The residue (13.9 g) was purified by column chromatography on silica gel eluting with a mixture of toluene and ethyl acetate (50:1). The crude product (1.3 g) was recrystallized from ethanol to give pale brown crystal of 2-(4-fluorophenyl)-3-[4-(methylsulfonyl)phenyl]-5-(trifluoromethyl)thiophene (1.04 g).

mp: 145°–146° C.

IR (Nujol): 1600, 1510 cm$^{-1}$

NMR (DMSO-d$_6$, δ): 3.20 (3H, s), 7.1–8.0 (9H, m)

Mass (m/z): 400 (M$^+$), 321

The following compounds (Examples 5-1) and 5-2)) were obtained according to a similar manner to that of Example 4.

EXAMPLE 5

1) 2-(4-Fluorophenyl)-3-(4-nitrophenyl)-5-(trifluoromethyl)thiophene mp: 103°–107° C.

IR (Nujol): 1600, 1560, 1510 cm$^{-1}$

Mass (m/z): 367 (M$^+$)

2) 2-(4-Fluorophenyl)-3-[4-(methylsulfonyl)phenyl]-5-(pentafluoroethyl)thiophene mp: 183°–185° C.

IR (Nujol): 1600, 1550, 1510 cm$^{-1}$

NMR (DMSO-d$_6$, δ): 3.25 (3H, s), 7.1–8.0 (9H, m)

Mass (m/z): 450 (M$^+$)

EXAMPLE 6

Titanium (IV) chloride (2.7 ml) was added dropwise to a stirred solution of 2-(4-fluorophenyl)-3-[4-(methylsulfonyl)phenyl]thiophene (5 g) and acetyl chloride (2.2 ml) in benzene (50 ml) at 5° to 10° C. The mixture was stirred at ambient temperature for 4 hours, poured into ice-water, and extracted with ethyl acetate. The extract was washed with an aqueous solution of sodium bicarbonate, dried and concentrated. The residue was recrystallized from a mixture of ethanol and ethyl acetate to give pale brown crystals of 5-acetyl-2-(4-fluorophenyl)-3-[4-(methylsulfonyl)phenyl]thiophene (3.7 g).

mp: 169°–172° C.

IR (Nujol): 1670, 1600, 1510 cm$^{-1}$

NMR (DMSO-d$_6$, δ): 2.58 (3H, s), 3.21 (3H, s), 7.0–8.0 (3H, m), 8.11 (1H, s)

Mass (m/z): 374 (M$^+$), 359

The following compounds (Examples 7-1) to 7-11)) were obtained according to a similar manner to that of Example 6.

EXAMPLE 7

1) 5-Acetyl-2-(4-fluorophenyl)-3-(4-nitrophenyl)thiophene mp: 225°–227° C.

IR (Nujol): 1660, 1600, 1545, 1510 cm$^{-1}$

NMR (DMSO-d$_6$, δ): 2.61 (3H, s), 7.2–7.5 (4H, m), 7.56 (2H, d, J=8 Hz), 8.20 (1H, s), 8.22 (2H, d, J=8 Hz)

Mass (m/z): 341 (M$^+$), 326

2) 5-Acetyl-2-(4-fluorophenyl)-3-(4-methoxyphenyl)thiophene mp: 114°–115° C.

IR (Nujol): 1650, 1610, 1550, 1510 cm$^{-1}$

NMR (CDCl$_3$, δ): 2.58 (3H, s), 3.82 (3H, s), 6.8–7.4 (8H, m), 7.67 (1H, s)

Mass (m/z): 326 (M$^+$)

3) 5-Acetyl-2,3-bis(4-fluorophenyl)thiophene mp: 134°–135° C.

IR (Nujol): 1645, 1610, 1550, 1510 cm$^{-1}$

NMR (CDCl$_3$, δ): 2.59 (3H, s), 6.9–7.3 (8H, m), 7.67 (1H, s)

Mass (m/z): 314 (M$^+$), 299

4) 5-Acetyl-2-(4-methoxyphenyl)-3-[4-(methylsulfonyl)phenyl]thiophene mp: 141°–143° C.

IR (Nujol): 1655, 1600, 1540, 1510 cm$^{-1}$

NMR (CDCl$_3$, δ): 2.59 (3H, s), 3.68 (3H, s), 3.83 (3H, s), 6.8–8.0 (9H, m)

Mass (m/z): 386 (M$^+$)

5) 2-(4-Methoxyphenyl)-3-[4-(methylthio)phenyl]-5-propionylthiophene

IR (Film): 1660, 1605, 1510 cm$^{-1}$

NMR (CDCl$_3$, δ): 1.24 (3H, t, J=7 Hz), 2.44 (3H, s), 2.89 (2H, q, J=7 Hz), 3.79 (3H, s), 6.4–7.3 (8H, m), 7.58 (1H, s)

6) 5-Acetyl-2-(4-chlorophenyl)-3-[4-(methylthio)phenyl]thiophene

IR (Film): 1660, 1595, 1535, 1490 cm$^{-1}$

NMR (CDCl$_3$, δ): 2.44 (3H, s), 2.53 (3H, s), 7.0–7.6 (9H, m)

7) 5-Acetyl-3-[4-(ethylthio)phenyl]-2-(4-fluorophenyl)thiophene mp: 70°–72° C.

IR (Nujol): 1670, 1600, 1540, 1510 cm$^{-1}$

Mass (m/z): 356 (M$^+$)

8) 5-Acetyl-2-(3,4-difluorophenyl)-3-[4-(methylthio)phenyl]thiophene mp: 100°–104° C.

IR (Nujol): 1675, 1600, 1540, 1515 cm$^{-1}$

Mass (m/z): 360 (M$^+$)

9) 5-[3,5-Di(t-butyl)-4-hydroxybenzoyl]-2-(4-fluorophenyl)-3-[4-(methylsulfonyl)phenyl]thiophene mp: 168°–172° C.

IR (Nujol): 3550, 1625, 1595, 1535, 1510 cm$^{-1}$

NMR (DMSO-d$_6$, δ): 1.44 (18H, s), 3.22 (3H, s), 7.0–8.0 (12H, m)

Mass (m/z): 564 (M$^+$)

10) 5-Acetyl-3-[4-(methylthio)phenyl]-2-(4-nitrophenyl)thiophene

IR (Film): 1660, 1595, 1515 cm$^{-1}$

Mass (m/z): 369 (M$^+$)

11) 5-Acetyl-2-(4-methoxyphenyl)-3-[4-(methylthio)phenyl]thiophene

IR (Film): 1660, 1610, 1515 cm$^{-1}$

NMR (CDCl$_3$, δ): 2.43 (3H, s), 2.57 (3H, s), 3.80 (3H, s), 6.7–7.3 (8H, m), 7.66 (1H, s)

Mass (m/z): 354 (M$^+$)

EXAMPLE 8

A solution of 2-(4-fluorophenyl)-3-[4-(methylthio)phenyl]thiophene (1.0 g) and trifluoroacetic anhydride (2 ml) in dichloroethane (5 ml) was heated in a steel bomb at 120° C. overnight. The mixture was washed with an aqueous solution of sodium bicarbonate and water, dried and concentrated under reduced pressure. The residue was purified by column chromatography on silica gel eluting with a mixture of hexane and toluene (2:1) to give yellow crystals of 2-(4-fluorophenyl)-3-[4-(methylthio)phenyl]-5-(trifluoroacetyl)thiophene (0.87 g).

IR (Film): 1690, 1600, 1535, 1510 cm$^{-1}$

NMR (CDCl$_3$, δ): 2.52 (3H, s), 6.8–7.5 (8H, m), 7.95 (1H, s)

Mass (m/z): 396 (M$^+$)

EXAMPLE 9

A mixture of 5-acetyl-2-(4-fluorophenyl)-3-[4-(methylsulfonyl)phenyl]thiophene (1 g), thallium(III) nitrate trihydrate (1.4 g) and perchloric acid (70%; 3 ml) in methanol (15 ml) and dioxane (7 ml) was stirred at ambient temperature for 7 hours. The insoluble material was filtered. The filtrate was diluted with water and extracted with chloroform. The extract was dried over magnesium sulfate and concentrated to give an oil of methyl 5-(4-fluorophenyl)-4-[4-(methylsulfonyl)phenyl]thiophene-2-acetate (1.2 g).

IR (Film): 1740, 1670, 1600, 1510 cm$^{-1}$

NMR (CDCl$_3$, δ): 3.30 (3H, s), 3.81 (3H, s), 3.91 (2H, s), 6.9–8.0 (9H, m)

mass (m/z): 404 (M$^+$), 345

EXAMPLE 10

A mixture of methyl 5-(4-fluorophenyl)-4-[4-(methylsulfonyl)phenyl]thiophene-2-acetate (2 g) and 4N sodium hydroxide solution (3.7 ml) in tetrahydrofuran (20 ml) as stirred at ambient temperature for 1 hour. The mixture was diluted with water and washed with toluene. The aqueous layer was acidified with hydrochloric acid and extracted with ethyl acetate. The extract was washed with water, dried and concentrated. The residue was recrystallized from a mixture of ethanol and water to give pale orange crystals of 5-(4-fluorophenyl)-4-[4-(methylsulfonyl)phenyl]thiophene-2-acetic acid (1.6 g).

mp: 171°–173° C.

IR (Nujol): 1700, 1600, 1510 cm$^{-1}$

NMR (DMSO-d$_6$, δ): 3.24 (3H, s), 3.93 (2H, s), 7.1–8.0 (9H, m)

Mass (m/z): 390 (M$^+$), 345

EXAMPLE 11

A mixture of ethyl 5-(4-fluorophenyl)-4-(4-methoxyphenyl)thiophene-2-carboxylate (2.3 g) and potassium hydroxide (640 mg) in methanol (20 ml) was refluxed overnight. The solvent was evaporated, and the residue was dissolved in water, acidified and extracted with chloroform. The extract was washed with water, dried over magnesium sulfate and concentrated to dryness. The residue was washed with ethanol to give crystals of 5-(4-fluorophenyl)-4-(4-methoxyphenyl)thiophene-2-carboxylic acid (1.7 g).

mp: 204°–206° C.

IR (Nujol): 1675, 1605, 1545, 1515 cm$^{-1}$

NMR (DMSO-$d_6$, δ): 3.75 (3H, s), 6.8–7.5 (8H, m), 7.73 (1H, s), 11.2 (1H, s)

Mass (m/z): 328 (M$^+$)

The following compounds (Examples 12-1) to 12-8)) were obtained according to a similar manner to that of Example 11.

EXAMPLE 12

1) 5-(2,4-Difluorophenyl)-4-[4-(methylthio)phenyl]thiophene-2-carboxylic acid.
mp: 193°–194° C.
IR (Nujol): 1680, 1620, 1595, 1540 cm$^{-1}$ 2) 5-(3,4-Difluorophenyl)-4-[4-(methylthio)phenyl]thiophene-2-carboxylic acid.
mp: 148°–151° C.
IR (Nujol): 2600, 1670, 1600, 1545 cm$^{-1}$
NMR (DMSO-$d_6$, δ): 2.47 (3H, s), 7.1–7.6 (7H, m), 7.78 (1H, s), 13.3 (1H, s)
Mass (m/z): 362 (M$^+$)

3) 4,5-Bis(4-fluorophenyl)thiophene-2-carboxylic acid
mp: 201°–203° C.
IR (Nujol): 2600, 1670, 1600, 1550, 1510 cm$^{-1}$
NMR (DMSO-$d_6$, δ): 7.1–7.4 (8H, m), 7.78 (1H, s), 13.32 (1H, s)
Mass (m/z): 316 (M$^+$)

4) 4,5-Bis[4-(methylthio)phenyl]thiophene-2-carboxylic acid
mp: 224°–227° C.
IR (Nujol): 2500, 1670, 1590, 1535 cm$^{-1}$ 5) 5-(4-Methoxyphenyl)-4-[4-(methylthio)phenyl]thiophene-2-carboxylic acid.
mp: 225°–226° C.
IR (Nujol): 1670, 1610, 1540 cm$^{-1}$ 6) 4-(4-Fluorophenyl)-5-[4-(methylthio)phenyl]thiophene-2-carboxylic acid
mp: 179°–181° C.
IR (Nujol): 1665, 1595, 1510 cm$^{-1}$ 7) 5-(4-Chlorophenyl)-4-[4-(methylthio)phenyl]thiophene-2-carboxylic acid
mp: 203°–205° C.
IR (Nujol): 1680, 1535, 1495 cm$^{-1}$
NMR (DMSO-$d_6$, δ): 2.49 (3H, s), 7.2–7.5 (8H, m), 7.78 (1H, s)
Mass (m/z): 360 (M$^+$)

8) 4-[4-(Ethylthio)phenyl]-5-(4-fluorophenyl)thiophene-2-carboxylic acid
mp: 160°–162° C.
IR (Nujol): 2600, 1675, 1600, 1540 cm$^{-1}$
NMR (DMSO-$d_6$, δ): 1.24 (3H, t, J=7 Hz), 2.98 (2H, q, J=7 Hz), 7.1–7.4 (8H, m), 7.78 (1H, s), 13.27 (1H, s)
Mass (m/z): 358 (M$^+$)

EXAMPLE 13

A mixture of 5-(4-fluorophenyl)-4-[4-(methylsulfonyl)phenyl]thiophene-2-acetic acid (4.1 g) and 1,1'-carbonyldiimidazole (1.8 g) in tetrahydrofuran (50 ml) was stirred and refluxed for 1 hour. The mixture was added dropwise to an ice-cooled mixture of ammonia water (28%; 5 ml) and tetrahydrofuran (10 ml). The resulting mixture was stirred overnight, diluted with water, and extracted with ethyl acetate. The extract was washed with an aqueous solution of sodium bicarbonate, water, and dilute hydrochloric acid, successively. The organic layer was dried and concentrated, and the residue was recrystallized from a mixture of chloroform, ethyl acetate and ethanol to give crystals of 5-(4-fluorophenyl)-4-[4-(methylsulfonyl)phenyl]thiophene-2-acetamide (3.2 g).

mp: 215°–216° C.

IR (Nujol): 3450, 3350, 1660, 1510 cm$^{-1}$

NMR (DMSO-$d_6$, δ): 3.23 (3H, s), 3.72 (2H, s), 7.0–8.0 (11H, m)

Mass (m/z): 389 (M$^+$), 345

EXAMPLE 14

A mixture of 5-(4-fluorophenyl)-4-[4-(methylsulfonyl)phenyl]thiophene-2-carboxylic acid (7.1 g) and phosphorus pentachloride (4.1 g) in toluene (100 ml) and tetrahydrofuran (25 ml) was stirred at ambient temperature for 1 hour. The mixture was concentrated to dryness to give pale yellow crystals of 5-(4-fluorophenyl)-4-[4-(methylsulfonyl)phenyl]thiophene-2-carbonyl chloride (8.1 g).

IR (Film): 1750, 1600, 1540, 1510 cm$^{-1}$ 5-(4-Fluorophenyl)-4-[4-(methylsulfonyl)phenyl]thiophene-2-carbonyl chloride (1.4 g) was added to a stirred mixture of methylamine (25% in water, 2 ml), tetrahydrofuran (15 ml) and water (5 ml) at 5° C. The mixture was stirred at room temperature for 2 hours, diluted with ethyl acetate, washed with water, and concentrated to dryness. The residue was purified by column chromatography on silica gel (20 g) eluting with a mixture of chloroform and ethyl acetate (1:1). The purified powder (1.1 g) was crystallized from diethyl ether to give colorless crystals of N-methyl-5-(4-fluorophenyl)-4-[4-(methylsulfonyl)phenyl]thiophene-2-carboxamide (1.0 g).

mp: 169°–170° C.

IR (Nujol): 3450, 1650, 1600, 1550, 1510 cm$^{-1}$

NMR (DMSO-$d_6$, δ): 2.83 (3H, d, J=4 Hz), 3.36 (3H, s), 7.2–8.3 (9H, m), 8.4–8.8 (1H, m)

Mass (m/z): 389 (M$^+$), 359

The following compounds (Examples 15-1) to 15-27)) were obtained according to a similar manner to that of Example 14.

EXAMPLE 15

1) 5-(4-Fluorophenyl)-4-[4-(methylsulfonyl)phenyl]thiophene-2-carboxamide
mp: 233°–234° C.
IR (Nujol): 3480, 3200, 1675, 1600, 1510 cm$^{-1}$
NMR (DMSO-$d_6$, δ): 3.28 (3H, s), 7.2–8.1 (11H, m),
Mass (m/z): 375 (M$^+$), 357

2) N-Methyl-4,5-bis(4-methoxyphenyl)thiophene-2-carboxamide
mp: 161°–162° C.
IR (Nujol): 3350, 1625, 1560, 1510 cm$^{-1}$
NMR (DMSO-$d_6$, δ): 2.78 (3H, d, J=4.5 Hz), 3.76 (6H, s), 6.8–7.0 (4H, m), 7.1–7.3 (4H, m), 7.76 (1H, s), 8.47 (1H, q, J=4.5 Hz)
Mass (m/z): 353 (M$^+$)

3) N-Methyl-5-(4-fluorophenyl)-4-(4-nitrophenyl)thiophene-2-carboxamide
mp: 224°–226° C.
IR (Nujol): 3440, 1645, 1600, 1550, 1525, 1505 cm$^{-1}$
NMR (DMSO-d$_6$, δ): 2.81 (3H, d, J=4.5 Hz), 7.1–7.6 (6H, m), 7.94 (1H, s), 8.23 (2H, d, J=9 Hz), 8.62 (1H, q, J=4.5 Hz)
Mass (m/z): 356 (M$^+$), 326

4) N,N-Dimethyl-5-(4-fluorophenyl)-4-(4-nitrophenyl)thiophene-2-carboxamide
IR (Film): 1620, 1600, 1545, 1505 cm$^{-1}$ 5) 5-(4-Fluorophenyl)-4-(4-nitrophenyl)thiophene-2-carboxamide
mp: 223°–225° C.
IR (Nujol): 3500, 3400, 1670, 1600, 1550, 1505 cm$^{-1}$ 6) N,N-Dimethyl-5-(4-fluorophenyl)-4-(4-methoxyphenyl)thiophene-2-carboxamide
mp: 95°–96° C.
IR (Nujol): 1620, 1605, 1550, 1515, 1490 cm$^{-1}$
NMR (DMSO-d$_6$, δ): 3.16 (6H, s), 3.75 (3H, s), 6.8–7.4 (8H, m), 7.53 (1H, s)
Mass (m/z): 354, 311

7) N-Methyl-5-(4-fluorophenyl)-4-(4-methoxyphenyl)thiophene-2-carboxamide
mp: 162°–163° C.
IR (Nujol): 3380, 1620, 1550, 1500 cm$^{-1}$
NMR (CDCl$_3$, δ): 3.0 (3H, d, J=6 Hz), 3.75 (3H, s), 6.2 (1H, s), 6.7–7.3 (8H, m), 7.4 (1H, s)
Mass (m/z): 341 (M$^+$)

8) N-Methyl-4,5-bis(4-fluorophenyl)thiophene-2-carboxamide
mp: 182°–183° C.
IR (Nujol): 3330, 1615, 1570, 1505 cm$^{-1}$
NMR (CDCl$_3$, δ): 3.01 (3H, d, J=5 Hz), 6.12 (1H, q, J=5 Hz), 6.9–7.3 (8H, m), 7.49 (1H, s)
Mass (m/z): 329 (M$^+$), 299

9) N,N-Dimethyl-4,5-bis(4-fluorophenyl)thiophene-2-carboxamide
mp: 119°–120° C.
IR (Nujol) 1620, 1550, 1510 cm$^{-1}$
NMR (CDCl$_3$, δ): 3.24 (6H, s), 6.9–7.3 (8H, m), 7.36 (1H, s)
Mass (m/z): 343 (M$^+$), 299

10) N-Methyl-4,5-bis[4-(methylthio)phenyl]thiophene-2-carboxamide
mp: 141°–142° C.
IR (Nujol): 3250, 1630, 1560, 1545 cm$^{-1}$
NMR (CDCl$_3$, δ) 2.44 (6H, s), 2.97 (3H, d, J=5 Hz), 6.19 (1H, q, J=5 Hz), 6.9–7.5 (9H, m)
Mass (m/z): 385 (M$^+$)

11) N,N-Dimethyl-4,5-bis[4-(methylthio)phenyl]thiophene-2-carboxamide
IR (Film) 1610, 1535, 1490 cm$^{-1}$
NMR (CDCl$_3$, δ): 2.42 (6H, s), 3.17 (6H, s), 7.0–7.4 (9H, m)

12) N-Methyl-5-(4-methoxyphenyl)-4-[4-(methylthio)phenyl]thiophene-2-carboxamide
IR (Film): 3300, 1630, 1610, 1560, 1510 cm$^{-1}$
NMR (CDCl$_3$, δ): 2.43 (3H, s), 2.97 (3H, d, J=5 Hz), 3.76 (3H, s), 6.5–7.3 (9H, m), 7.50 (1H, s)

13) N,N-Dimethyl-5-(4-methoxyphenyl)-4-[4-(methylthio)phenyl]thiophene-2-carboxamide
IR (Film): 1610, 1540, 1500 cm$^{-1}$
NMR (CDCl$_3$, δ): 2.44 (3H, s), 3.19 (6H, s), 3.75 (3H, s), 6.6–7.3 (9H, m)

14) N,N-Dimethyl-5-(2,4-difluorophenyl)-4-[4-(methylthio)phenyl]thiophene-2-carboxamide
IR (Film): 1620, 1545, 1500 cm$^{-1}$
NMR (CDCl$_3$, δ): 2.44 (3H, s), 3.19 (6H, s), 6.6–7.4 (8H, m)

15) N-Methyl-4-(4-fluorophenyl)-5-[4-(methylthio)phenyl]thiophene-2-carboxamide
mp: 205°–206° C.
IR (Nujol): 3340, 1620, 1565, 1550, 1500 cm$^{-1}$ 16) N,N-Dimethyl-4-(4-fluorophenyl)-5-[4-(methylthio)phenyl]thiophene-2-carboxamide
mp: 121°–123° C.
IR (Nujol): 1620, 1510 cm$^{-1}$
Mass (m/z): 371 (M$^+$)

17) N-Methyl-5-(4-chlorophenyl)-4-[4-(methylthio)phenyl]thiophene-2-carboxamide
mp: 168°–169° C.
IR (Nujol): 3340, 1630, 1560 cm$^{-1}$
Mass (m/z): 373 (M$^+$)

18) N,N-Dimethyl-5-(4-chlorophenyl)-4-[4-(methylthio)phenyl]thiophene-2-carboxamide
mp: 137°–138° C.
IR (Nujol): 1620, 1600 cm$^{-1}$
NMR (DMSO-d$_6$, δ): 2.45 (3H, s), 3.17 (6H, s), 7.1–7.6 (9H, m)
Mass (m/z): 387 (M$^+$)

19) N-Methyl-4-[4-(ethylthio)phenyl]-5-(4-fluorophenyl)thiophene-2-carboxamide
IR (Film): 3300, 1640, 1625, 1565, 1545, 1500 cm$^{-1}$
(CDCl$_3$, δ): 1.28 (3H, t, J=7 Hz), 2.89 (2H, q, J=7 Hz), 2.96 (3H, d, J=6 Hz), 6.44 (1H, q, J=6 Hz), 6.7–7.3 (8H, m), 7.46 (1H, s)

20) N,N-Dimethyl-4-[4-(ethylthio)phenyl]-5-(4-fluorophenyl)thiophene-2-carboxamide
IR (Film): 1620, 1540, 1500 cm$^{-1}$
NMR (CDCl$_3$, δ): 1.31 (3H, t, J=7 Hz), 2.92 (2H, q, J=7 Hz), 3.19 (6H, s), 6.8–7.5 (9H, m)

21) N,N-Dimethyl-5-(3,4-difluorophenyl)-4-[4-(methylthio)phenyl]thiophene-2-carboxamide
IR (Film): 1620, 1545, 1500 cm$^{-1}$ 22) N-Methyl-5-(4-fluorophenyl)-4-[4-(methylthio)phenyl]thiophene-2-carboxamide
mp: 98°–100° C.
IR (Nujol): 3300, 1630, 1600, 1565, 1505 cm$^{-1}$
NMR (DMSO-d$_6$, δ): 2.47 (3H, s), 2.79 (1H, d, J=4 Hz), 7.1–7.5 (8H, m), 7.83 (1H, s), 8.54 (1H, q, J=4 Hz)
Mass (m/z): 357 (M$^+$)

23) N-Isopropyl-5-(4-fluorophenyl)-4-[4-(methylsulfonyl)phenyl]thiophene-2-carboxamide
mp: 160°–164° C.
IR (Nujol): 3380, 1645, 1600, 1555, 1510 cm$^{-1}$
NMR (DMSO-d$_6$, δ): 1.18 (6H, d, J=9 Hz), 3.12 (3H, s), 4.0–4.2 (1H, m), 7.1–7.6 (6H, m), 7.90 (2H, d, J=8 Hz), 8.02 (1H, s), 8.36 (1H, d, J=9 Hz)
Mass (m/z): 417 (M$^+$)

24) N-Hydroxy-N-methyl-5-(4-fluorophenyl)-4-[4-(methylsulfonyl)phenyl]thiophene-2-carboxamide
mp: 95°–98° C.
IR (Nujol): 1600, 1540, 1510 cm$^{-1}$
NMR (DMSO-d$_6$, δ): 3.24 (3H, s), 3.32 (3H, 7.2–8.0 (9H, m), 10.78 (1H, s)
Mass (m/z): 405 (M$^+$)

25) N-{5-(4-Fluorophenyl)-4-[4-(methylsulfonyl)phenyl]-2-thenoyl}-N-methylglycine ethyl ester
mp: 148°–151° C.
IR (Nujol): 1750, 1630 cm$^{-1}$
NMR (DMSO-d$_6$, δ): 1.21 (3H, t, J=7 Hz), 3.24 (3H, s), 3.40 (3H, s), 4.16 (2H, q, J=7 Hz), 4.27 (2H, s), 7.1–8.0 (9H, m)

26) N-Hydroxy-N-methyl-5-(4-fluorophenyl)-4-[4-(methylsulfonyl)phenyl]thiophene-2-acetamide mp: 99°–103° C.

IR (Nujol): 1630, 1600, 1510 cm$^{-1}$

NMR (DMSO-d$_6$, δ): 3.15 (3 H, s), 3.22 (3H, s), 4.00 (2H, s), 7.1–8.0 (9H, m), 10.2 (1H, s)

Mass (m/z): 419 (M$^+$)

27) N,N-Dimethyl-5-(2-fluorophenyl)-4-[4-(methylthio)phenyl]thiophene-2-carboxamide IR (Film): 1620, 1600, 1545, 1500 cm$^{-1}$ Mass (m/z): 371 (M$^+$)

EXAMPLE 16

A mixture of 5-(4-fluorophenyl)-4-[4-(methylsulfonyl)phenyl]thiophene-2-sulfonic acid (10.5 g) and thionyl chloride (20 ml) was refluxed for 1 hour. The mixture was concentrated to dryness. The residue was dissolved in ethyl acetate, washed with ice-water, dried and concentrated to give a brown oil (8.7 g).

A solution of the oil in tetrahydrofuran (45 ml) was added to ammonia water (15 ml) at 5° C. The mixture was stirred for 1 hour and extracted with chloroform. The extract was dried and concentrated. The residual oil was purified by column chromatography on silica gel (120 g) eluting with a mixture of toluene and ethyl acetate (3:1) to give an oil (1.2 g). The purified oil was crystallized from diethyl ether to give pale brown crystals of 5-(4-fluorophenyl)-4-[4-(methylsulfonyl)phenyl]thiophene-2-sulfonamide (0.76 g).

mp: 195°–197° C.

IR (Nujol): 3340, 3250, 1600 cm$^{-1}$

NMR (DMSO-d$_6$, δ): 3.30 (3H, s), 7.0–8.1 (11H, m)

Mass (m/z): 411 (M$^+$)

EXAMPLE 17

A mixture of 5-(4-fluorophenyl)-4-[4-(methylsulfonyl)phenyl]thiophene-2-carboxylic acid (1.0 g) and 1,1'-carbonyldiimidazole (0.45 g) in tetrahydrofuran (15 ml) was refluxed for 1.5 hours. 5-Aminotetrazole (0.226 g) was added and the mixture was refluxed for 3 hours. The mixture was diluted with water (50 ml), acidified with hydrochloric acid, and cooled in an ice-water bath. The precipitates were collected and recrystallized from ethanol to give colorless crystals of N-(5-tetrazolyl)-5-(4-fluorophenyl)-4-[4-(methylsulfonyl)phenyl]thiophene-2-carboxamide (0.93 g).

mp: 269°–271° C. (dec.)

IR (Nujol): 3200, 1670, 1600, 1545, 1510 cm$^{-1}$

NMR (DMSO-d$_6$, δ): 3.30 (3H, s), 7.1–8.1 (8H, m), 8.56 (1H, s)

Mass (m/z): 443 (M$^+$)

The following compounds (Examples 18-1) to 18-9)) were obtained according to a similar manner to that of Example 17.

EXAMPLE 18

1) N,N-Dimethyl-5-(4-fluorophenyl)-4-[4-(methylsulfonyl)phenyl]thiophene-2-carboxamide mp: 172°–173° C.

IR (Nujol): 1605, 1545, 1490 cm$^{-1}$

NMR (DMSO-d$_6$, δ): 3.21 (3H, s), 3.27 (6H, s), 7.0–8.1 (9H, m) Mass (m/z): 403 (M$^+$), 359

2) N-Phenyl-5-(4-fluorophenyl)-4-[4-(methylsulfonyl)phenyl]thiophene-2-carboxamide mp: 227°–228° C.

IR (Nujol): 1660, 1545 cm$^{-1}$

NMR (DMSO-d$_6$, δ): 3.28 (3H, s), 7.0–8.4 (14H, m), 10.35 (1H, s)

Mass (m/z): 450, 359

3) N-(2,2,2-Trifluoroethyl)-5-(4-fluorophenyl)-4-[4-(methylsulfonyl)phenyl]thiophene-2-carboxamide mp: 201°–203° C.

IR (Nujol): 3400, 1660, 1600, 1555, 1530, 1510 cm$^{-1}$

NMR (DMSO-d$_6$, δ): 3.27 (3H, s), 4.0–4.5 (2H, m), 7.2–8.2 (9H, m), 9.27 (1H, t, J=6 Hz)

Mass (m/z): 457 (M$^+$), 359

4) N,N-Dimethyl-5-(4-fluorophenyl)-4-[4-(methylthio)phenyl]thiophene-2-carboxamide IR (Film): 2920, 1620, 1600, 1530 cm$^{-1}$ NMR (CDCl$_3$, δ): 2.51 (3H, s), 3.28 (6H, s), 6.8–7.5 (9H, m)

Mass (m/z): 371 (M$^+$), 327

5) N,N-Dimethyl-4,5-bis(4-methoxyphenyl)thiophene-2-carboxamide mp: 79°–81° C.

IR (Nujol): 1630, 1610, 1550, 1515 cm$^{-1}$

NMR (CDCl$_3$, δ): 3.23 (6H, s), 3.80 (6H, s), 6.7–6.9 (4H, m), 7.1–7.3 (4H, m), 7.35 (1H, s)

Mass (m/z): 367 (M$^+$)

6) N-Ethyl-5-(4-fluorophenyl)-4-[4-(methylsulfonyl)phenyl]thiophene-2-carboxamide mp: 149°–151° C.

IR (Nujol): 3400, 1640, 1555, 1510 cm$^{-1}$

NMR (DMSO-d$_6$, δ): 1.14 (3H, t, J=7 Hz), 3.25 (3H, s), 3.2–3.4 (2H, m), 7.1–7.6 (6H, m), 7.90 (2H, d, J=8 Hz), 7.96 (1H, s), 8.60 (1H, t, J=6 Hz)

Mass (m/z): 403 (M$^+$)

7) N-{5-(4-Fluorophenyl)-4-[4-(methylsulfonyl)phenyl]-2-thenoyl}morpholine mp: 158°–161° C.

IR (Nujol): 1620, 1600, 1545, 1510 cm$^{-1}$

NMR (DMSO-d$_6$, δ): 3.24 (3H, s), 3.6–3.8 (8H, m), 7.1–8.0 (9H, m)

Mass (m/z): 445 (M$^+$), 359

8) 1-{5-(4-Fluorophenyl)-4-[4-(methylsulfonyl)phenyl]-2-thenoyl}-4-methylpiperazine mp: 68°–72° C.

IR (Nujol): 1610, 1545, 1510 cm$^{-1}$

NMR (DMSO-d$_6$, δ): 2.12 (3H, s), 2.37 (4H, broad s), 3.23 (3H, s), 3.72 (4H, broad s), 7.1–8.0 (9H, m)

Mass (m/z): 458 (M$^+$)

9) N-(N,N-Dimethylaminoethyl)-5-(4-fluorophenyl)-4-[4-(methylsulfonyl)phenyl]thiophene-2-carboxamide mp: 218°–221° C.

IR (Nujol): 2600, 2470, 1640, 1595, 1550, 1510 cm$^{-1}$

NMR (DMSO-d$_6$, δ): 2.83 (6H, s), 3.25 (3H, s), 3.2–3.8 (4H, m), 7.2–8.3 (9H, m), 9.34 (1H, t, J=6 Hz)

EXAMPLE 19

To an ice-cooled mixture of 5-(4-fluorophenyl)-4-[4-(methylsulfonyl)phenyl]thiophene-2-acetamide (2.6 g) and diethyl oxalate (0.97 ml) in N,N-dimethylformamide (18 ml) was added potassium t-butoxide (0.84 g). The mixture was stirred at 0° C. for 15 minutes. Potassium t-butoxide (0.87 g) was added to the resulting mixture, and the mixture was stirred at 0° C. for 1 hour and at ambient temperature overnight.

The mixture was poured into ice-water (130 ml) and acidified with hydrochloric acid. The precipitates were collected, washed with water, dried, and purified by column chromatography on silica gel (100 g) eluting with a mixture of chloroform and methanol (5:1). The obtained product was dissolved in a mixture of ethanol and ethyl acetate. The solution was filtered and the filtrate was concentrated. The residue was triturated with chloroform to give red brown crystals of 2-{5-(4-fluorophenyl)-4-[4-(methylsulfonyl)phenyl]-2-thienyl}-3-hydroxymaleimide potassium salt (1.6 g).

mp: 305°–310° C. (dec.)

IR (Nujol): 3400, 1745, 1700, 1610, 1510 cm$^{-1}$

NMR (DMSO-d$_6$, δ): 3.20 (3H, s), 7.0–7.9 (9H, m), 9.40 (1H, s)

EXAMPLE 20

A mixture of 5-(4-fluorophenyl)-4-[4-(methylthio)phenyl]thiophene-2-carboxylic acid (10.8 g) and hydrogen peroxide (30%, 9.3 ml) in acetic acid (108 ml) was stirred at 70° C. for 3 hours. The mixture was cooled in an ice-water bath, and the precipitates were collected and washed with ethanol to give pale yellow crystals of 5-(4-fluorophenyl)-4-[4-(methylsulfonyl)phenyl]thiophene-2-carboxylic acid (8.1 g).

mp: 264°–264.5° C.

IR (Nujol): 1680, 1600, 1545, 1510 cm$^{-1}$

NMR (DMSO-d$_6$, δ): 3.28 (3H, s), 7.1–8.1 (9H, m)

Mass (m/z): 376 (M$^+$)

EXAMPLE 21

A mixture of 2-(4-fluorophenyl)-3-[4-(methylthio)phenyl]-5-(trifluoroacetyl)thiophene (0.79 g) and m-chloroperbenzoic acid (1 g) in dichloromethane (13 ml) was stirred overnight at room temperature. The insoluble was filtered, and the filtrate was washed with an aqueous solution of sodium bicarbonate, dried and concentrated. The residue (0.91 g) was recrystallized from ethanol to give pale brown crystals of 2-(4-fluorophenyl)-3-[4-(methylsulfonyl)phenyl]-5-(trifluoroacetyl)thiophene (0.73 g).

mp: 199°–201° C.

IR (Nujol): 1685, 1600, 1510 cm$^{-1}$

NMR (DMSO-d$_6$, δ): 3.22 (3H, s), 7.1–8.3 (9H, m)

Mass (m/z): 428 (M$^+$), 359

The following compounds (Examples 22-1) to 22-19)) were obtained according to a similar manner to that of Example 21.

EXAMPLE 22

1) N-Methyl-4,5-bis[4-(methylsulfonyl)phenyl]thiophene-2-carboxamide mp: 234°–236° C.

IR (Nujol): 3400, 1650, 1595, 1500, 1525 cm$^{-1}$

NMR (DMSO-d$_6$, δ): 2.81 (3H, d, J=5 Hz), 3.26 (3H, s), 7.5–8.0 (9H, m), 8.65 (1H, q, J=5 Hz)

Mass (m/z): 449 (M$^+$)

2) N,N-Dimethyl-4,5-bis[4-(methylsulfonyl)phenyl]thiophene-2-carboxamide mp: 245°–247° C.

IR (Nujol): 1620, 1590, 1500 cm$^{-1}$

NMR (DMSO-d$_6$, δ): 3.26 (12H, s), 7.5–8.0 (9H, m)

Mass (m/z): 463 (M$^+$), 419

3) N-Methyl-5-(4-methoxyphenyl)-4-[4-(methylsulfonyl)phenyl]thiophene-2-carboxamide mp: 150°–151° C.

IR (Nujol): 3430, 1640, 1560, 1510 cm$^{-1}$

NMR (CDCl$_3$, δ): 3.0 (3H, d, J=5 Hz), 3.03 (3H, s), 3.75 (3H, s), 6.33 (1H, q, J=5 Hz), 6.7–7.8 (9H, m)

Mass (m/z): 401 (M$^+$)

4) N,N-Dimethyl-5-(4-methoxyphenyl)-4-[4-(methylsulfonyl)phenyl]thiophene-2-carboxamide mp: 168°–169° C.

IR (Nujol): 1615, 1545, 1510 cm$^{-1}$

NMR (DMSO-d$_6$, δ): 3.17 (6H, s), 3.24 (3H, s), 3.77 (3H, s), 6.9–7.9 (9H, m)

Mass (m/z): 415 (M$^+$), 371

5) 2-(4-Methoxyphenyl)-3-[4-(methylsulfonyl)phenyl]-5-propionylthiophene mp: 154°–155° C.

IR (Nujol): 1655, 1605, 1510 cm$^{-1}$

NMR (CDCl$_3$, δ): 1.28 (3H, t, J=7 Hz), 2.97 (2H, q, J=7 Hz), 3.07 (3H, s), 3.83 (3H, s), 6.7–8.0 (9H, m)

Mass (m/z): 400 (M$^+$), 371

6) N-Methyl-5-(4-chlorophenyl)-4-[4-(methylsulfonyl)phenyl]thiophene-2-carboxamide mp: 196°–197° C.

IR (Nujol): 3400, 1650, 1635, 1550 cm$^{-1}$

NMR (CDCl$_3$, δ): 3.03 (3H, d, J=5 Hz), 3.08 (3H, s), 6.18 (1H, q, J=5 Hz), 7.1–7.9 (9H, m)

Mass (m/z): 405 (M$^+$)

7) N,N-Dimethyl-5-(4-chlorophenyl)-4-[4-(methylsulfonyl)phenyl]thiophene-2-carboxamide mp: 165°–166° C.

IR (Nujol): 1620, 1540, 1500 cm$^{-1}$

NMR (CDCl$_3$, δ): 3.0 (3H, s), 3.25 (6H, s), 7.1–8.0 (9H, m)

Mass (m/z): 419 (M$^+$)

8) 5-Acetyl-2-(4-chlorophenyl)-3-[4-(methylsulfonyl)phenyl]thiophene mp: 159°–160° C.

IR (Nujol): 1675, 1595, 1540 cm$^{-1}$

NMR (DMSO-d$_6$, δ): 2.61 (3H, s), 3.25 (3H, s), 7.3–8.0 (8H, m), 8.18 (1H, s)

Mass (m/z): 390 (M$^+$)

9) N-Methyl-4-[4-(ethylsulfonyl)phenyl]-5-(4-fluorophenyl)thiophene-2-carboxamide mp: 181°–183° C.

IR (Nujol): 3400, 1650, 1600, 1555, 1510 cm$^{-1}$

NMR (DMSO-d$_6$, δ): 1.11 (3H, t, J=7 Hz), 2.80 (3H, d, J=5 Hz), 3.31 (2H, q, J=7 Hz), 7.1–8.0 (9H, m), 8.58 (1H, q, J=5 Hz)

Mass (m/z): 4.03 (M$^+$)

10) N,N-Dimethyl-4-[4-(ethylsulfonyl)phenyl]-5-(4-fluorophenyl)thiophene-2-carboxamide mp: 104°–105° C.

IR (Nujol): 1620, 1600, 1545, 1500 cm$^{-1}$

NMR (CDCl$_3$, δ): 1.30 (3H, t, J=7 Hz), 3.10 (2H, q, J=7 Hz), 3.23 (6H, s), 6.8–7.9 (9H, m)

Mass (m/z): 417 (M$^+$)

11) 5-Acetyl-3-[4-(ethylsulfonyl)phenyl]2-(4-fluorophenyl)thiophene mp: 128°–129° C.

IR (Nujol): 1670, 1600, 1510 cm$^{-1}$

NMR (CDCl$_3$, δ): 1.30 (3H, t, J=7 Hz), 2.60 (3H, s), 3.14 (2H, g, J=7 Hz), 6.9–7.9 (9H, m)

Mass (m/z): 388 (M$^+$)

12) N,N-Dimethyl-5-(3,4-difluorophenyl)-4-[4-(methylsulfonyl)phenyl]thiophene-2-carboxamide mp: 112°–113° C.

IR (Nujol): 1620, 1600, 1545, 1500 cm$^{-1}$

NMR (CDCl$_3$, δ): 3.03 (3H, s), 3.20 (6H, s), 6.9–8.0 (8H, m)

Mass (m/z): 421 (M$^+$)

13) 5-Acetyl-2-(3,4-difluorophenyl)-3-[4-(methylsulfonyl)phenyl]thiophene mp: 150°–151° C.

IR (Nujol): 1675, 1600, 1535, 1510 cm$^{-1}$

NMR (CDCl$_3$, δ): 2.61 (3H, s), 3.09 (3H, 7.0–8.0 (8H, m)

Mass (m/z): 392 (M$^+$)

14) N,N-Diethyl-5-(4-fluorophenyl)-4-[4-(methylsulfonyl)phenyl]-2-thenylamine mp: 98°–102° C.

IR (Nujol): 1600, 1510 cm$^{-1}$

NMR (DMSO-d$_6$, δ): 1.20 (6H, t, J=7 Hz), 3.0–3.3 (4H, m), 3.23 (3H, s), 4.52 (2H, s), 7.1–7.9 (9H, m)

Mass (m/z): 417 (M$^+$), 345

15) N-Methyl-N-propyl-5-(4-fluorophenyl)-4-[4-(methylsulfonyl)phenyl]-2-thenylamine mp: 128°–130° C.

IR (Nujol): 1600, 1510 cm$^{-1}$

NMR (DMSO-d$_6$, δ): 0.88 (3H, t, J=7 Hz), 1.6–2.0 (2H, m), 2.96 (3H, s), 3.0–3.3 (2H, m), 3.23 (3H, s), 4.59 (2H, ABq, J=13 Hz), 7.1–7.9 (9H, m)

Mass (m/z): 417 (M$^+$), 345

16) N-Methyl-4-(4-fluoromethyl-5-[4-(methylsulfonyl)phenyl]thiophene-2-carboxamide mp: 280°–281° C.

IR (Nujol): 3400, 1630, 1560, 1505 cm$^{-1}$

NMR (CDCl$_3$, δ): 3.04 (3H, d, J=5 Hz), 3.07 (3H, 6.0 (1H, m), 6.9–7.9 (9H, m)

Mass (m/z): 389 (M$^+$), 359

17) N,N-Dimethyl-4-(4-fluorophenyl)-5-[4-(methylsulfonyl)phenyl]thiophene-2-carboxamide mp: 192°–193° C.

IR (Nujol) 1610, 1545, 1510 cm$^{-1}$

NMR (CDCL$_3$, δ): 3.07 (3H, s), 3.25 (6H, s), 6.9–7.9 (9H, m)

Mass (m/z): 403 (M$^+$), 359

18) Ethyl 4-[4-(methylsulfonyl)phenyl]-5-(4-nitrophenyl)thiophene-2-carboxylate mp: 158°–160° C.

IR (Nujol): 1705, 1595, 1515 cm$^{-1}$

NMR (CDCl$_3$, δ): 1.40 (3H, t, J=7 Hz), 3.10 (3H, s), 4.38 (2H, q, J=7 Hz), 7.4–8.3 (9H, m)

Mass (m/z): 431 (M$^+$)

19) N,N-Dimethyl-5-(2-fluorophenyl)-4-[4-(methylsulfonyl)phenyl]thiophene-2-carboxamide mp: 155°–158° C.

IR (Nujol): 1620, 1600, 1545 cm$^{-1}$

NMR (CDCl$_3$, δ): 3.06 (3H, s), 3.26 (6H, s), 6.9–7.9 (9H, m)

Mass (m/z): 403 (M$^+$)

EXAMPLE 23

A mixture of N,N-dimethyl-5-(4-fluorophenyl)-4-[4-(methylthio)phenyl]-2-thenylamine (1.4 g) and m-chloroperbenzoic acid (2.6 g) in dichloromethane (25 ml) was stirred overnight. The insoluble was filtered. The filtrate was washed with an aqueous solution of sodium bicarbonate, dried and concentrated. The residue was dissolved in 30% hydrogen chloride in methanol (1 ml) and methanol was evaporated. The residue was pulverized with diethyl ether to give a pale yellow powder of N,N-dimethyl-5-(4-fluorophenyl)-4-[4-(methylsulfonyl)phenyl]-2-thenylamine hydrochloride (1.4 g).

mp: 192°–194° C.

IR (Nujol): 3400, 2550, 1600, 1510 cm$^{-1}$

NMR (DMSO-d$_6$, δ): 3.23 (3H, s), 3.55 (6H, s), 5.25 (2H, s), 7.2–8.1 (9H, m)

Mass (m/z): 389 (M$^+$), 345

The following compounds (Examples 24-1) to 24-7)) were obtained according to a similar manner to that of Example 23.

EXAMPLE 24

1) N,N-Dimethyl-4,5-bis[4-(methylsulfonyl)phenyl]-2-thenylamine hydrochloride mp: 215°–217° C. (dec.)

IR (Nujol): 2500, 1590, 1535 cm$^{-1}$

NMR (DMSO-d$_6$, δ): 3.26 (6H, s), 3.53 (6H, s), 5.23 (2H, s), 7.5–8.0 (9H, m), 13.07 (1H, s)

Mass (m/z): 449 (M$^+$), 405

2) N,N-Dimethyl-5-(4-methoxyphenyl)-4-[4-(methylsulfonyl)phenyl]-2-thenylamine hydrochloride mp: 206°–208° C. (dec.)

IR (Nujol): 2550, 1600, 1535, 1515 cm$^{-1}$

NMR (DMSO-d$_6$, δ): 3.24 (3H, s), 3.51 (6H, s), 3.77 (3H, s), 5.17 (2H, s), 6.9–8.0 (9H, m)

Mass (m/z): 401 (M$^+$), 357

3) N,N-Dimethyl-5-(3,4-difluorophenyl)-4-[4-(methylsulfonyl)phenyl]-2-thenylamine hydrochloride mp: 181°–183° C. (dec.)

IR (Nujol): 2530, 1600, 1520 cm$^{-1}$

NMR (DMSO-d$_6$, δ): 3.24 (3H, s), 3.52 (6H, s), 5.19 (2H, s), 7.1–8.0 (8H, m), 13.0 (1H, s)

Mass (m/z): 407 (M$^+$), 363

4) 2-(4-Fluorophenyl)-3-[4-(methylsulfonyl)phenyl]-5-(1-pyrrolidinylmethyl)thiophene hydrochloride mp: >250° C.

IR (Nujol): 2600, 1600, 1545, 1510 cm$^{-1}$

NMR (DMSO-d$_6$, δ): 2.17 (4H, s), 3.24 (3H, s), 3.90 (4H, s), 5.33 (2H, s), 7.2–8.0 (9H, m), 12.75 (1H, s)

5) N-Ethyl-N-methyl-5-(4-fluorophenyl)-4-[4-(methylsulfonyl)phenyl]-2-thenylamine hydrochloride mp: 95°–100° C. (dec.)

IR (Nujol): 1600, 1510 cm$^{-1}$

NMR (DMSO-d$_6$, δ): 1.40 (3H, t, J=8 Hz), 3.20 (3H, s), 3.37 (3H, s), 3.77 (2H, q, J=8 Hz), 5.15 (2H, s), 7.1–8.0 (9H, m)

Mass (m/z): 403 (M$^+$), 344

6) N,N-Dimethyl-5-(4-chlorophenyl)-4-[4-(methylsulfonyl)phenyl]-2-thenylamine hydrochloride mp: 181°–183° C.

IR (Nujol): 2550, 1600, 1535 cm$^{-1}$

NMR (DMSO-d$_6$, δ): 3.25 (3H, s), 3.52 (6H, s), 5.21 (2H, s), 7.2–8.0 (9H, m), 13.06 (1H, s)

Mass (m/z): 405 (M$^+$), 361

7) N,N-Dimethyl-4-[4-(ethylsulfonyl)phenyl]-5-(4-fluorophenyl)-2-thenylamine hydrochloride mp: 175°–177° C. (dec.)

IR (Nujol): 2500, 1600, 1510 cm$^{-1}$

NMR (DMSO-d$_6$, δ): 1.11 (3H, t, J=7 Hz), 3.31 (2H, q, J=7 Hz), 3.53 (6H, s), 5.21 (2H, s), 7.1–7.9 (9H, m), 13.04 (1H, s)

Mass (m/z): 403 (M$^+$)

EXAMPLE 25

A mixture of N-(benzyloxycarbonyl)-5-(4-fluorophenyl)-4-[4-(methylthio)phenyl]-2-thenylamine (1.3 g) and m-chloroperbenzoic acid (80%; 1.3 g) in dichloromethane (20 ml) was stirred at ambient temperature for 3 hours. The insoluble was filtered. The filtrate was washed with an aqueous solution of sodium bicarbonate, dried and concentrated. The residue (1.4 g) was purified by column chromatography on silica gel eluting with a mixture of toluene and ethyl acetate (5:1) to give an oil (0.78 g). The oil was dissolved in 30% hydrogen bromide in acetic acid. The solution was stirred at ambient temperature for 1 hour and concentrated in vacuo. The residue was washed with isopropyl ether to give white powder of 5-(4-fluorophenyl)-4-[4-(methylsulfonyl)[henyl]-2-thenylamine hydrobromide (0.7 g).

mp: >200° C.

IR (Nujol): 1600, 1510 cm$^{-1}$

NMR (DMSO-d$_6$, δ): 3.24 (3H, s), 4.32 (2H, s), 7.1–7.5 (7H, m), 7.80 (2H, d, J=8 Hz), 8.37 (2H, broad s)

Mass (m/z): 361 (M$^+$)

The following compounds (Examples 26-1) and 26-2)) were obtained according to a similar manner to that of Example 25.

EXAMPLE 26

1) N-Methyl-5-(4-fluorophenyl)-4-[4-(methylsulfonyl)phenyl]-2-thenylamine hydrobromide mp: 100°–110° C. (dec.)

IR (Nujol): 1600, 1510 cm$^{-1}$

NMR (DMSO-d$_6$, δ): 2.64 (3H, s), 3.24 (3H, s), 4.44 (2H, s), 7.2–7.6 (7H, m), 7.90 (2H, d, J=8 Hz), 9.00 (2H, broad s), Mass (m/z): 375 (M$^+$)

2) N-Ethyl-5-(4-fluorophenyl)-4-[4-(methylsulfonyl)phenyl]-2-thenylamine hydrochloride mp: 100°–105° C.

IR (Nujol): 1600, 1510 cm$^{-1}$

NMR (DMSO-d$_6$, δ): 1.35 (3H, t, J=6 Hz), 3.0–3.2 (2H, m), 3.45 (3H, s), 4.4–4.7 (2H, m), 7.1–8.0 (9H, m)

Mass (m/z): 389 (M$^+$)

EXAMPLE 27

A mixture of N-methyl-5-(4-fluorophenyl)-4-[4-(methylthio)phenyl]thiophene-2-carboxamide (1.66 g), sodium periodate (1.05 g) and water (1 ml) in methanol (100 ml) was stirred at 0° C. for 2 days. The insoluble was filtered and the filtrate was evaporated. The residue was extracted with dichloromethane. The extract was washed with water, dried over magnesium sulfate and concentrated to dryness. The residue was recrystallized from ethanol to give colorless crystals of N-methyl-5-(4-fluorophenyl)-4-[4-(methylsulfinyl)phenyl]thiophene-2-carboxamide (1.1 g).

mp: 218°–220° C.

IR (Nujol): 3300, 1640, 1550, 1500 cm$^{-1}$

NMR (DMSO-d$_6$, δ): 2.77 (3H, s), 2.80 (3H, d, J=4 Hz), 7.1–7.7 (8H, m), 7.89 (1H, s), 8.56 (1H, q, J=4 Hz)

Mass (m/z): 373 (M$^+$), 358

EXAMPLE 28

A mixture of N,N-dimethyl-5-(4-fluorophenyl)-4-[4-(methylthio)phenyl]-2-thenylamine (1 g), sodium periodate (1.07 g) and water (5 ml) in methanol (50 ml) was stirred at ambient temperature for 2 hours. The insoluble was filtered and the filtrate was evaporated. The residue was dissolved in dichloromethane, washed with an aqueous solution of sodium bicarbonate and water, dried and concentrated in vacuo. The oily residue (1 g) was purified by column chromatography on silica gel eluting with a mixture of chloroform and methanol (10:1). The obtained oil (0.9 g) was dissolved in a solution of hydrogen chloride in ethanol (10 ml) and the solution was concentrated. The residue was washed with diethyl ether to give white powder of N,N-dimethyl-5-(4-fluorophenyl)-4-[4-(methylsulfinyl)phenyl]-2-thenylamine hydrochloride (0.76 g).

mp: 212°–216° C.

IR (Nujol): 2520, 2480, 1600, 1510 cm$^{-1}$

NMR (DMSO-d$_6$, δ): 2.76 (6H, s), 2.78 (3H, s), 4.54 (2H, s), 7.1–7.7 (9H, m), 11.22 (1H, s)

Mass (m/z): 373 (M$^+$)

EXAMPLE 29

A mixture of 5-(4-fluorophenyl)-4-[4-(methylthio)phenyl]thiophene-2-carbaldehyde (2.2 g) and m-chloroperbenzoic acid (3.62 g) in dichloromethane (32 ml) was stirred for 8 hours at ambient temperature. The insoluble was filtered, and the filtrate was washed with an aqueous solution of sodium bicarbonate, dried and concentrated. The residual oil (2 g) was purified by column chromatography on silica gel (150 g) eluting with a mixture of toluene and ethyl acetate (10:1) to give a pale brown powder of 2-(4-fluorophenyl)-5-hydroxy-3-[4-(methylsulfonyl)phenyl]thiophene (1.1 g).

mp: 60° C.

IR (CHCl$_3$): 1675, 1605, 1565, 1510 cm$^{-1}$

NMR (DMSO-d$_6$, δ): 3.20 (3H, s), 6.74 (1H, s), 6.9–8.0 (9H, m)

Mass (m/z): 348 (M$^+$)

EXAMPLE 30

A mixture of 5-acetyl-2-(4-fluorophenyl)-3-[4-(methylsulfonyl)phenyl]thiophene (1 g) and sodium borohydride (0.12 g) in methanol (19 ml) was stirred at ambient temperature for 2 hours. Acetic acid (1 ml) was added and the mixture was concentrated. The residue was dissolved in ethyl acetate, washed with water and an aqueous solution of sodium bicarbonate, dried and concentrated. The residue was recrystallized from a mixture of hexane and ethyl acetate to give crystals of 2-(4-fluorophenyl)-5-(1-hydroxyethyl)-3-[4-(methylsulfonyl)phenyl]thiophene (0.74 g).

mp: 103°–105° C.

IR (Nujol): 3400, 1600, 1510 cm$^{-1}$

NMR (CDCl$_3$, δ): 1.65 (3H, d, J=7 Hz), 2.10 (1H, d, J=4 Hz), 3.0 (3H, s), 5.0–5.3 (1H, m), 6.8–7.9 (9H, m)

Mass (m/z): 376 (M$^+$), 361

EXAMPLE 31

A mixture of 5-(4-fluorophenyl)-4-[4-(methylsulfonyl)phenyl]thiophene-2-carbonyl chloride (1.2 g) and sodium borohydride (0.21 g) in dioxane (15 ml) was stirred at ambient temperature for 2 hours. The mixture was diluted with ethyl acetate, washed with water, dilute hydrochloric acid, an aqueous solution of sodium bicarbonate, successively, dried and concentrated. The residue (1.2 g) was recrystallized from ethanol to give pale brown crystals of 5-(4-fluorophenyl)-4-[4-(methylsulfonyl)phenyl]thiophene-2-methanol (0.55 g).

mp: 140°–142° C.

IR (Nujol): 3400, 1600, 1515 cm$^{-1}$

NMR (DMSO-d$_6$, δ): 3.20 (3H, s), 4.65 (2H, d, J=5 Hz), 5.56 (1H, t, J=5 Hz), 7.0–7.9 (9H, m)

Mass (m/z): 362 (M$^+$)

EXAMPLE 32

A mixture of methyl 5-(4-fluorophenyl)-4-[4-(methylsulfonyl)phenyl]thiophene-2-acetate (1.8 g) and lithium aluminum hydride (0.63 g) in diethyl ether (30 ml) was stirred at 0° C. for 1 hour. Ethyl acetate and 10% sulfuric acid (50 ml) were added, and the resulting mixture was filtered. The organic layer was separated, washed with water, dried and concentrated under reduced pressure. The residual pale yellow oil (1.6 g) was purified by column chromatography on silica gel eluting with a mixture of toluene and ethyl acetate (2:1). The obtained oil (1.4 g) was pulverized with hexane to give a yellow powder of 2-(4-fluorophenyl)-5-(2-hydroxyethyl)-3-[4-(methylsulfonyl)phenyl]thiophene.

mp: 102°–108° C.

IR (Nujol): 3500, 1600, 1510 cm$^{-1}$

NMR (DMSO-d$_6$, δ): 2.97 (2H, t, J=6 Hz), 3.22 (3H, s), 3.6–3.8 (2H, m), 4.90 (1H, t, J=5 Hz), 7.0–7.9 (9H, m)

Mass (m/z): 376 (M$^+$)

EXAMPLE 33

A mixture of 5-acetyl-2-(4-fluorophenyl)-3-[4-(methylsulfonyl)phenyl]thiophene (1.35 g), methoxyamine hydrochloride (0.45 g) and pyridine (0.44 ml) in dioxane (17 ml) was stirred at ambient temperature for 1 hour. The mixture was concentrated, and the residue was triturated with water, filtered, washed with water and dried. The crude crystals were recrystallized from ethyl acetate to give pure crystals of 2-(4-fluorophenyl)-5-[-1-(methoxyimino)ethyl]-3-[4-(methylsulfonyl)phenyl]thiophene (0.68 g).

mp: 200°–203° C.

IR (Nujol): 1600, 1550, 1510 cm$^{-1}$

NMR (DMSO-d$_6$, δ): 2.24 (3H, s), 3.20 (3H, s), 3.90 (3H, s), 7.0–8.0 (9H, m)

Mass (m/z): 403 (M$^+$)

The following compound (Example 34) was obtained according to a similar manner to that of Example 33.

EXAMPLE 34

5-[3,5-Di(t-butyl)-4-hydroxy-α-(hydroxyimino)benzyl]-2-(4-fluorophenyl)-3-[4-(methylsulfonyl)phenyl]thiophene mp: 235°–237° C.

IR (Nujol): 3630, 3400, 1600, 1510 cm$^{-1}$

NMR (DMSO-d$_6$, δ): 1.42 (18H, s), 3.23 (3H, s), 7.1–8.0 (12H, m)

Mass (m/z): 563, 548

EXAMPLE 35

Nitric acid (d=1.42; 1.6 ml) was added dropwise to a stirred solution of 2-(4-fluorophenyl)-3-[4-(methylsulfonyl)phenyl]thiophene (6 g) in acetic anhydride (98 ml) at −5° to 0° C. The mixture was stirred for 1 hour at 0° C., treated with sodium bicarbonate (1 g), and concentrated under reduced pressure. The residue was dissolved in ethyl acetate, washed with water and an aqueous solution of sodium bicarbonate, and concentrated. The residue was purified by column chromatography on silica gel eluting with a mixture of toluene and ethyl acetate (20:1) to give yellow crystals of 2-(4-fluorophenyl)-3-[4-(methylsulfonyl)phenyl]-5-nitrothiophene (4.4 g).

mp: 155°–156° C.

IR (Nujol): 3100, 1600, 1510 cm$^{-1}$

NMR (DMSO-d$_6$, δ): 3.28 (3H, s), 7.1–8.1 (8H, m), 8.42 (1H, s)

Mass (m/z): 377 (M$^+$)

The following compound (Example 36) was obtained according to a similar manner to that of Example 35.

EXAMPLE 36

2,3-Bis(4-methoxyphenyl)-5-nitrothiophene

IR (Film): 1610, 1510, 1500 cm$^{-1}$

EXAMPLE 37

A mixture of 2-(4-fluorophenyl)-3-[4-(methylsulfonyl)phenyl]-5-nitrothiophene (3.6 g), iron powder (3.6 g) and ammonium chloride (0.36 g) in ethanol (58 ml) and water (22 ml) was stirred and refluxed for 1 hour. The insoluble was filtered and washed with N,N-dimethylformamide (40 ml). The filtrate was concentrated. The residue was triturated with water, filtered, and washed with water and ethanol to give a pale yellow powder of 5-(4-fluorophenyl)-4-[4-(methylsulfonyl)phenyl]-2-thiophenamine (2.7 g).

mp: 207°–209° C.

IR (Nujol): 3450, 3350, 1600, 1510 cm$^{-1}$

Mass (m/z): 347 (M$^+$)

The following compounds (Examples 38-1) to 38-12)) were obtained according to a similar manner to that of Example 37.

EXAMPLE 38

1) 4,5-Bis(4-methoxyphenyl)-2-thiophenamine
   IR (Film): 3440, 3370, 1610, 1510 cm$^{-1}$ 2) N,N-Dimethyl-4-(4-aminophenyl)-5-(4-fluorophenyl)thiophene-2-carboxamide
   IR (Film): 3470, 3370, 3230, 1610, 1550, 1515, 1490 cm$^{-1}$
   NMR (DMSO-d$_6$, δ): 3.15 (6H, s), 5.20 (2H, s), 6.50 (2H, d, J=8.5 Hz), 6.93 (2H, d, J=8.5 Hz), 7.1–7.5 (5H, m)
   Mass (m/z): 340 (M$^+$)

3) 4-(4-Aminophenyl)-5-(4-fluorophenyl)thiophene-2-carboxamide
   mp: 172°–174° C.
   IR (Nujol): 3350, 3170, 1675, 1600, 1515 cm$^{-1}$
   NMR (DMSO-d$_6$, δ): 5.24 (2H, s), 6.51 (2H, d, J=8 Hz), 6.90 (2H, d, J=8 Hz), 7.1–7.5 (5H, m), 7.80 (1H, s), 8.00 (1H, s)
   Mass (m/z): 312 (M$^+$)

4) N-Methyl-4-(4-aminophenyl)-5-(4-fluorophenyl)thiophene-2-carboxamide
   mp: 222°–223° C.
   IR (Nujol): 3450, 3330, 1625, 1570, 1510 cm$^{-1}$
   NMR (DMSO-d$_6$, δ): 2.78 (3H, d, J=4.5 Hz), 5.21 (2H, s), 6.4–7.4 (8H, m), 7.74 (1H, s), 8.48 (1H, q, J=4.5 Hz)
   Mass (m/z): 326 (M$^+$)

5) 3-(4-Aminophenyl)-2-(4-fluorophenyl)-5-(trifluoromethyl)thiophene
   mp: 114°–116° C.
   IR (Nujol): 3500, 3400, 1630, 1610, 1520 cm$^{-1}$
   Mass (m/z): 337 (M$^+$)

6) 5-Acetyl-3-(4-aminophenyl)-2-(4-fluorophenyl)thiophene
   IR (Film): 3480, 3380, 3230, 1650, 1620, 1550, 1515 cm$^{-1}$
   NMR (DMSO-d$_6$, δ): 2.57 (3H, s), 5.24 (2H, s), 6.51 (2H, d, J=8.5 Hz), 6.94 (2H, d, J=8.5 Hz), 7.1–7.5 (4H, m), 7.94 (1H, s)

7) Ethyl 5-(4-aminophenyl)-4-[4-(methylsulfonyl)phenyl]thiophene-2-carboxylate
   mp: 160°–165° C. (dec.)
   IR (Nujol): 3475, 3400, 3200, 1700, 1610, 1550 cm$^{-1}$ NMR (DMSO-d$_6$, δ): 1.25 (3H, t, J=7 Hz), 3.20 (3H, s), 4.30 (2H, q, J=7 Hz), 5.54 (2H, s), 6.4–7.9 (9H, m)

Mass (m/z): 401 (M$^+$)

8) 2-(4-Aminophenyl)-5-bromo-3-[4-(methylsulfonyl)phenyl]thiophene mp: 185°–190° C. (dec.)

IR (Nujol): 3475, 3400, 1620, 1610, 1600, 1515 cm$^{-1}$

NMR (DMSO-d$_6$, δ): 3.22 (3H, s), 5.43 (2H, s), 6.50 (2H, d, J=8 Hz), 6.89 (2H, d, J=8 Hz), 7.39 (1H, s), 7.51 (2H, d, J=8 Hz), 7.84 (2H, d, J=8 Hz)

Mass (m/z): 408, 406

9) 2-(4-Aminophenyl)-5-chloro-3-[4-(methylthio)phenyl]thiophene mp: 205°–210° C. (dec.)

IR (Nujol): 1610, 1515 cm$^{-1}$ 10) 2-(4-Aminophenyl)-5-bromo-3-[4-(methylthio)phenyl]thiophene IR (Nujol): 3400, 1610, 1515 cm$^{-1}$ 11) 5-Acetyl-2-(4-aminophenyl)-3-[4-(methylthio)phenyl]thiophene IR (Nujol): 3500, 3400, 1655, 1610, 1515 cm$^{-1}$ 12) Ethyl 5-(4-aminophenyl)-4-[4-(methylthio)phenyl]thiophene-2-carboxylate mp: 155°–158° C.

IR (Nujol): 3500, 3400, 1685, 1630, 1610 cm$^{-1}$

Mass (m/z): 369 (M$^+$)

EXAMPLE 39

A mixture of 5-(4-fluorophenyl)-4-[4-(methylsulfonyl)phenyl]-2-thiophenamine (1.0 g) and methanesulfonyl chloride (0.27 ml) in pyridine (10 ml) was stirred overnight. Pyridine was evaporated, and the residue was dissolved in ethyl acetate, washed with water, dried and concentrated. The residue was dissolved in tetrahydrofuran (10 ml) and treated with 4N sodium hydroxide (1.8 ml) for 2 hours. Ethyl acetate and water were added and the mixture was separated. The aqueous layer was acidified and extracted with ethyl acetate. The extract was dried and concentrated to dryness. The residue (1.1 g) was purified by column chromatography on silica gel eluting with a mixture of toluene and ethyl acetate (3:1) to give a pale brown powder of N-{5-(4-fluorophenyl)-4-[4-(methylsulfonyl)phenyl]-2-thienyl}methanesulfonamide (0.79 g).

mp: 87°–90° C.

IR (Nujol): 3200, 1600, 1510 cm$^{-1}$

NMR (DMSO-d$_6$, δ): 3.17 (3H, s), 3.26 (3H, s), 6.98 (1H, s), 7.1–8.0 (8H, m), 10.4 (1H, broad s)

Mass (m/z): 425 (M$^+$), 346

The following compounds (Examples 40-1) to 40-7)) were obtained according to a similar manner to that of Example 39.

EXAMPLE 40

1) N-[4,5-Bis(4-methoxyphenyl)-2-thienyl]methanesulfonamide

IR (Film): 3250, 1610, 1515 cm$^{-1}$

NMR (CDCl$_3$, δ): 3.12 (3H, s), 3.79 (6H, s), 6.5–7.3 (10H, m)

Mass (m/z): 389 (M$^+$), 310

2) N-Methyl-5-(4-fluorophenyl)-4-[4-(methylsulfonylamino)phenyl]thiophene-2-carboxamide mp: 233°–235° C.

IR (Nujol): 3430, 3270, 1650, 1610, 1555, 1510 cm$^{-1}$

NMR (DMSO-d$_6$, δ): 2.78 (3H, d, J=4.5 Hz), 3.0 (3H, s), 7.0–7.5 (8H, m), 7.78 (1H, s), 8.47 (1H, q, J=4.5 Hz), 9.81 (1H, s)

Mass (m/z): 404 (M$^+$), 325

3) N,N-Dimethyl-5-(4-fluorophenyl)-4-[4-(methylsulfonylamino)phenyl]thiophene-2-carboxamide mp: 163°–165° C.

IR (Nujol): 3210, 1615, 1605, 1545, 1510 cm$^{-1}$

NMR (DMSO-d$_6$, δ): 3.02 (3H, s), 3.16 (6H, s), 7.1–7.4 (8H, m), 7.55 (1H, s), 9.85 (1H, s)

Mass (m/z): 418 (M$^+$), 339

4) N,N-Dimethyl-5-(4-fluorophenyl)-4-[4-(methylsulfonylamino)phenyl]-2-thenylamine mp: 178°–180° C.

IR (Nujol): 3270, 1605, 1515 cm$^{-1}$

NMR (DMSO-d$_6$, δ): 2.23 (6H, s), 3.00 (3H, s), 3.61 (2H, s), 7.0–7.4 (9H, m), 9.83 (1H, s)

Mass (m/z): 404 (M$^+$), 360

5) 5-(4-Fluorophenyl)-4-[4-(methylsulfonylamino)phenyl]thiophene-2-carboxamide mp: 219°–220° C.

IR (Nujol): 3450, 3280, 3160, 1660, 1605, 1545, 1510 cm$^{-1}$

NMR (DMSO-d$_6$, δ): 3.03 (3H, s), 7.1–7.4 (8H, m), 7.50 (1H, s), 7.86 (1H, s), 8.03 (1H, s), 9.87 (1H, s)

Mass (m/z): 390 (M$^+$), 311

6) 4'-[2-(4-Fluorophenyl)-5-(trifluoromethyl)-3-thienyl]methanesulfonanilide mp: 150°–152° C.

IR (Nujol): 3320, 1600, 1560, 1510 cm$^{-1}$

NMR (DMSO-d$_6$, δ): 3.02 (3H, s), 7.1–7.5 (8H, m), 7.85 (1H, s), 9.90 (1H, s)

Mass (m/z): 415 (M$^+$), 336

7) 4'-[5-Acetyl-2-(4-fluorophenyl)-3-thienyl]methanesulfonanilide mp: 147°–149° C.

IR (Nujol): 3280, 1670, 1610, 1540, 1510 cm$^{-1}$

NMR (DMSO-d$_6$, δ): 2.58 (3H, s), 3.03 (3H, s), 7.1–7.5 (8H, m), 8.04 (1H, s), 9.89 (1H, s)

Mass (m/z): 389 (M$^+$), 310

EXAMPLE 41

A mixture of 5-(4-fluorophenyl)-4-[4-(methylsulfonyl)phenyl]-2-thiophenamine (1.2 g) and acetic anhydride (0.36 ml) in dichloromethane (12 ml) was stirred at ambient temperature for 2 hours, and concentrated under reduced pressure. The residue was purified by column chromatography on silica gel eluting with a mixture of toluene and ethyl acetate (3:1) to give a brown powder of N-{5-(4-fluorophenyl)-4-[4-(methylsulfonyl)phenyl]-2-thienyl}acetamide (0.77 g).

mp: 80°–92° C.

IR (Nujol): 3300, 1660, 1575, 1535, 1505 cm$^{-1}$

NMR (CDCl$_3$, δ): 2.27 (3H, s), 3.11 (3H, s), 6.68 (1H, s), 6.8–8.0 (8H, m), 8.77 (1H, s)

Mass (m/z): 389 (M$^+$), 347

EXAMPLE 42

Methyl chloroformate (0.23 ml) in acetonitrile (1 ml) was added dropwise to a stirred solution of 5-(4-fluorophenyl)-4-[4-(methylsulfonyl)phenyl]-2-thiophenamine (1.1 g) and pyridine (0.24 ml) in acetonitrile (8 ml) and tetrahydrofuran (10 ml) at −20° C. The mixture was stirred at 5° C. for 1 hour, diluted with ethyl acetate, washed with water, dried, and concentrated. The residue was purified by column chromatography on silica gel (30 g) eluting with a mixture of toluene and ethyl acetate (10:1). The product was recrystallized from ethanol to give pale red crystals of methyl N-{5-(4-fluorophenyl)-4-[4-(methylsulfonyl)phenyl]-2-thienyl}carbamate (0.84 g).

mp: 103°–108° C. (dec.)

IR (Nujol): 3330, 1720, 1600, 1580, 1540 cm$^{-1}$

NMR (DMSO-$d_6$, δ): 3.28 (3H, s), 3.80 (3H, s), 6.77 (1H, s), 7.2–8.1 (8H, m), 10.94 (1H, s)

Mass (m/z): 405 (M$^+$), 373

The following compounds (Examples 43-1) to 43-7)) were obtained according to a similar manner to that of Example 42.

EXAMPLE 43

1) N-{5-(4-Fluorophenyl)-4-[4-(methylsulfonyl)phenyl]-2-thienyl}-5-methyl-4-isoxazolecarboxamide
  mp: 236°–240° C.
  IR (Nujol): 3330, 1665, 1610, 1570, 1530 cm$^{-1}$
  NMR (DMSO-$d_6$, δ): 2.74 (3H, s), 3.24 (3H, s), 7.0 (1H, s), 7.2–8.0 (8H, m), 9.08 (1H, s), 11.42 (1H, s)
  Mass (m/z): 456 (M$^+$)

2) Methyl N-[4,5-bis(4-methoxyphenyl)-2-thienyl]carbamate
  mp: 109°–113° C.
  IR (Nujol): 3400, 1695, 1610, 1570, 1535, 1510 cm$^{-1}$
  NMR (CDCl$_3$, δ): 3.79 (6H, s), 3.82 (3H, s), 6.62 (1H, s), 6.7–6.9 (4H, m), 7.0–7.3 (5H, m)
  Mass (m/z): 369 (M$^+$), 337

3) N-(Benzyloxycarbonyl)-5-(4-fluorophenyl)-4-[4-(methylthio)phenyl]-2-thenylamine
  NMR (DMSO-$d_6$, δ): 2.45 (3H, s), 4.39 (2H, d, J=6 Hz), 5.14 (2H, s), 6.9–7.5 (14H, m), 8.00 (1H, t, J=6 Hz)
  Mass (m/z): 463 (M$^+$)

4) N-(Benzyloxycarbonyl)-N-methyl-5-(4-fluorophenyl)-4-[4-(methylthio)phenyl]-2-thenylamine
  NMR (DMSO-$d_6$, δ): 2.45 (3H, s), 2.93 (3H, s), 4.60 (2H, s), 5.14 (2H, s), 7.1–7.4 (14H, m)
  Mass (m/z): 477

5) N-{5-(4-Fluorophenyl)-4-[4-(methylsulfonyl)phenyl]-2-thienyl}-3,5-di(t-butyl)-4-hydroxybenzamide
  mp: >250° C.
  IR (Nujol): 3630, 3200, 1630, 1600, 1560, 1530, 1510 cm$^{-1}$
  NMR (DMSO-$d_6$, δ): 1.45 (18H, s), 3.23 (3H, s), 7.0–8.0 (13H, m)
  Mass (m/z): 579 (M$^+$)

6) Ethyl N-{5-(4-fluorophenyl)-4-[4-(methylsulfonyl)phenyl]-2-thienyl}carbamate
  mp: 70°–75° C.
  IR (Nujol): 3300, 1720, 1580, 1530 cm$^{-1}$
  NMR (DMSO-$d_6$, δ): 1.27 (3H, t, J=7 Hz), 3.22 (3H, s), 4.19 (2H, q, J=7 Hz), 6.67 (1H, s), 7.1–7.9 (8H, m), 10.91 (1H, s)
  Mass (m/z): 419 (M$^+$), 373

7) N-(Benzyloxycarbonyl)-N-ethyl-5-(4-fluorophenyl)-4-[4-(methylthio)phenyl]-2-thenylamine
  IR (Film): 1700, 1510, 1500 cm$^{-1}$
  NMR (CDCl$_3$, δ): 1.1–1.3 (3H, m), 2.47 (3H, s), 3.3–3.5 (2H, m), 4.60 (2H, s), 5.20 (2H, s), 6.9–7.4 (14H, m)

EXAMPLE 44

A mixture of 5-(4-fluorophenyl)-4-[4-(methylsulfonyl)phenyl]-2-thiophenamine (0.9 g) and methyl isocyanate (1.4 ml) in tetrahydrofuran (20 ml) was stirred and refluxed for 1 hour. The solvent was evaporated and the residue (1.5 g) was purified by column chromatography on silica gel eluting with a mixture of chloroform and methanol (10:1) to give a brown powder of N-{5-(4-fluorophenyl)-4-[4-(methylsulfonyl)phenyl]-2-thienyl}-N'-methylurea (0.77 g).

mp: 70°–75° C.

IR (Nujol): 3300, 1680, 1660, 1560, 1510 cm$^{-1}$

NMR (DMSO-$d_6$, δ): 2.66 (3H, d, J=4.5 Hz), 3.22 (3H, s), 6.30 (1H, q, J=4.5 Hz), 6.57 (1H, s), 7.1–7.3 (4H, m), 7.45 (2H, d, J=8 Hz), 7.84 (2H, d, J=8 Hz), 9.77 (1H, s)

Mass (m/z): 404 (M$^+$), 373

EXAMPLE 45

A solution of N,N-dimethyl-5-(4-fluorophenyl)-4-[4-(methylthio)phenyl]thiophene-2-carboxamide (1.95 g) in benzene (15 ml) was added dropwise to an ice-cooled mixture of lithium aluminum hydride (0.27 g) in diethyl ether (10 ml). The mixture was refluxed for 9 hours. To the mixture was added dropwise 4N sodium hydroxide solution. Ethyl acetate was added, and the mixture was filtered. The filtrate was washed with water, dried and evaporated. The oily residue (2 g) was purified by column chromatography on silica gel (20 g) eluting with a mixture of toluene and ethyl acetate (2:1) to give a yellow oil of N,N-dimethyl-5-(4-fluorophenyl)-4-[4-(methylthio)phenyl]-2-thenylamine (1.5 g).

IR (Film): 2770, 1600, 1510 cm$^{-1}$

NMR (CDCl$_3$, δ): 2.35 (6H, s), 2.50 (3H, s), 3.35 (2H, s), 6.8–7.5 (9H, m)

Mass (m/z): 357 (M$^+$), 313

The following compounds (Examples 46-1) to 46-9)) were obtained according to a similar manner to that of Example 45.

EXAMPLE 46

1) N,N-Dimethyl-4-(4-aminophenyl)-5-(4-fluorophenyl)-2-thenylamine
  IR (Film): 3400, 1620, 1515 cm$^{-1}$
  NMR (CDCl$_3$, δ): 2.34 (6H, s), 3.63 (2H, s), 3.66 (2H, s), 6.5–7.4 (9H, m)
  Mass (m/z): 326 (M$^+$), 282

2) N,N-Dimethyl-4,5-bis(4-fluorophenyl)-2-thenylamine
  mp: 93°–94° C.
  IR (Nujol): 1600, 1510 cm$^{-1}$
  NMR (CDCl$_3$, δ): 2.35 (6H, s), 3.64 (2H, s), 6.9–7.3 (9H, m)
  Mass (m/z): 329 (M$^+$), 285

3) N,N-Dimethyl-4,5-bis[4-(methylthio)phenyl]-2-thenylamine
  IR (Film): 1600, 1560, 1495 cm$^{-1}$ 4) N,N-Dimethyl-5-(4-methoxyphenyl)-4-[4-(methylthio)phenyl]-2-thenylamine
  IR (Film): 1610, 1575, 1515, 1500 cm$^{-1}$
  NMR (CDCl$_3$, δ): 2.33 (6H, s), 2.44 (3H, s), 3.58 (2H, s), 3.78 (3H, s), 6.6–7.3 (9H, m)

5) N,N-Dimethyl-5-(2,4-difluorophenyl)-4-[4-(methylthio)phenyl]-2-thenylamine
  mp: 95°–96° C.
  IR (Nujol): 1595, 1565, 1515, 1495 cm$^{-1}$
  NMR (CDCl$_3$, δ): 2.35 (6H, s), 2.46 (3H, s), 3.67 (2H, s), 6.7–7.3 (8H, m)
  Mass (m/z): 375 (M$^+$), 331

6) N,N-Dimethyl-5-(4-chlorophenyl)-4-[4-(methylthio)phenyl]-2-thenylamine

IR (Film): 1600, 1565, 1495 cm$^{-1}$

7) N,N-Dimethyl-4-[4-(ethylthio)phenyl]-5-(4-fluorophenyl)-2-thenylamine

IR (Film): 1600, 1510 cm$^{-1}$

Mass (m/z): 371 (M$^+$)

8) N,N-Dimethyl-5-(3,4-difluorophenyl)-4-[4-(methylthio)phenyl]-2-thenylamine

IR (Film): 1600, 1515, 1500 cm$^{-1}$

9) N-Methyl-5-(4-fluorophenyl)-4-[4-(methylthio)phenyl]-2-thenylamine

The following compounds (Examples 47-1) to 47-3)) were obtained by treating the compound as obtained according to a similar manner to that of Example 45 with a solution of hydrogen chloride in ethanol.

EXAMPLE 47

1) N,N-Dimethyl-4,5-bis(4-methoxyphenyl)thenylamine hydrochloride mp: 191°–195° C.

IR (Nujol): 3420, 2650, 1610, 1515 cm$^{-1}$

NMR (DMSO-d$_6$, δ): 2.76 (6H, s), 3.75 (6H, s), 4.49 (2H, s), 6.8–7.3 (8H, m), 7.45 (1H, s), 11.2 (1H, s)

Mass (m/z): 353 (M$^+$), 309

2) N,N-Dimethyl-5-(4-fluorophenyl)-4-(4-methoxyphenyl)-2-thenylamine hydrochloride mp: 214°–215° C.

IR (Nujol): 3400, 2460, 2370, 1610, 1560, 1510 cm$^{-1}$

NMR (D$_2$O, δ): 3.10 (6H, s), 3.70 (3H, s), 4.70 (2H, s), 6.7–7.4 (8H, m), 7.57 (1H, s)

Mass (m/z): 341 (M$^+$), 297

3) N,N-Dimethyl-5-(4-fluorophenyl)-4-[4-(methylthio)phenyl]-2-thenylamine hydrochloride mp: 160°–165° C.

IR (Nujol): 3400, 2500, 1600, 1510 cm$^{-1}$

NMR (DMSO-d$_6$, δ): 2.47 (3H, s), 2.77 (6H, s), 4.52 (2H, s), 7.1–7.4 (8H, m), 7.51 (1H, s), 11.27 (1H, s)

Mass (m/z): 357 (M$^+$)

The following compounds (Examples 48-1) to 48-5)) were obtained according to a similar manner to those of Examples 17 and 45.

EXAMPLE 48

1) 2-(4-Fluorophenyl)-3-[4-(methylthio)phenyl]-5-(1-pyrrolidinylmethyl)thiophene IR (Film): 1600, 1510 cm$^{-1}$ NMR (DMSO-d$_6$, δ): 1.6–1.8 (4H, m), 2.45 (3H, s), 2.4–2.6 (4H, m), 3.79 (2H, s), 7.0–7.3 (9H, m)

2) N-Ethyl-N-methyl-5-(4-fluorophenyl)-4-[4-(methylthio)phenyl]-2-thenylamine

IR (Film): 1600, 1510, 1500 cm$^{-1}$

NMR (DMSO-d$_6$, δ): 1.03 (3H, t, J=7 Hz), 2.21 (3H, s), 2.44 (3H, s), 2.44 (2H, q, J=7 Hz), 3.68 (2H, s), 7.0–7.3 (9H, m)

3) N,N-Diethyl-5-(4-fluorophenyl)-4-[4-(methylthio)phenyl]-2-thenylamine

IR (Film): 1600, 1510, 1500 cm$^{-1}$

NMR (DMSO-d$_6$, δ): 1.01 (6H, t, J=7 Hz), 2.45 (3H, s), 2.54 (4H, q, J=7 Hz), 3.76 (2H, s), 7.0–7.3 (9H, m)

Mass (m/z): 385 (M$^+$)

4) N-Methyl-N-propyl-5-(4-fluorophenyl)-4-[4-(methylthio)phenyl]-2-thenylamine

IR (Film): 1600, 1510, 1500 cm$^{-1}$

NMR (DMSO-d$_6$, δ): 0.87 (3H, t, J=7 Hz), 1.3–1.6 (2H, m), 2.21 (3H, s), 2.36 (2H, t, J=7 Hz), 2.46 (3H, s), 3.68 (2H, s), 7.0–7.4 (9H, m)

Mass (m/z): 385 (M$^+$), 313

5) N-Ethyl-5-(4-fluorophenyl)-4-[4-(methylthio)phenyl]-2-thenylamine

IR (Film): 1605, 1515 cm$^{-1}$

NMR (CDCl$_3$, δ): 1.17 (3H, t, J=7 Hz), 3.47 (3H, s), 2.78 (2H, q, J=7 Hz), 4.00 (2H, s), 6.9–7.4 (9H, m)

The following compound (Example 49) was obtained according to a similar manner to those of Examples 14 and 45.

EXAMPLE 49

5-(4-Fluorophenyl)-4-[4-(methylthio)phenyl]-2-thenylamine

NMR (DMSO-d$_6$, δ): 2.45 (3H, s), 3.82 (2H, s), 7.0–7.4 (9H, m)

EXAMPLE 50 n-Butyl lithium (1.6M) in hexane (36 ml) was added dropwise to a stirred solution of 2-(4-fluorophenyl)-3-[4-(methylsulfonyl)phenyl]thiophene (8.0 g) in tetrahydrofuran (80 ml) at −60° C. The mixture was stirred for 30 minutes, and N,N-dimethylformamide (3.7 ml) was added dropwise over ten minutes to the mixture. The mixture was stirred at −70° to −20° C. for 2 hours. 1N Hydrochloric acid (70 ml) was added dropwise, and the solution was extracted with ethyl acetate. The extract was washed with brine, dried and concentrated. The residual syrup was purified by column chromatography on silica gel eluting with a mixture of toluene and ethyl acetate (9:1). The obtained crystals (4.5 g) were recrystallized from ethyl acetate to give pale yellow crystals of 5-(4-fluorophenyl)-4-[4-(methylsulfonyl)phenyl]thiophene-2-carbaldehyde (3.7 g).

mp: 165°–166° C.

IR (Nujol): 1660, 1595, 1510 cm$^{-1}$

NMR (CDCl$_3$, δ): 3.09 (3H, s), 7.0–8.0 (9H, m), 9.94 (1H, s)

Mass (m/z): 360 (M$^+$)

The following compound (Example 51) was obtained according to a similar manner to that of Example 50.

EXAMPLE 51

5-(4-Fluorophenyl)-4-[4-(methylthio)phenyl]thiophene-2-carbaldehyde

IR (Film): 1670, 1600, 1540, 1510 cm$^{-1}$

NMR (CDCl$_3$, δ): 2.53 (3H, s), 6.9–7.6 (8H, m), 7.83 (1H, s), 10.0 (1H, s)

Mass (m/z): 328 (M$^+$)

EXAMPLE 52

Chlorosulfonic acid (5 ml) was added dropwise to a stirred powder of 2,3-bis(4-methoxyphenyl)thiophene (2.5 g) at ambient temperature. The mixture was stirred overnight and added to a mixture of ammonia water (31 ml), ethyl acetate and ice. The mixture was separated, and the organic layer was dried and concentrated. The residue was washed with ethanol to give pale brown crystals of 4,5-bis(4-methoxy-3-sulfamoylphenyl)thiophene-2-sulfonamide (0.62 g).

mp: 242°–244° C.

IR (Nujol): 3370, 3260, 1610, 1540, 1500 cm$^{-1}$

NMR (DMSO-d$_6$, δ): 3.89 (3H, s), 3.91 (3H, s), 7.1–7.9 (13H, m)

Mass (m/z): 533 (M$^+$), 454

EXAMPLE 53

2-(4-Fluorophenyl)-3-[4-(methylsulfonyl)phenyl]thiophene (1.1 g) was added portionwise to chlorosulfonic acid (1 ml), and the mixture was stirred at ambient temperature for 1 hour. The mixture was added to a mixture of 25% methylamine aqueous solution (20 ml) and tetrahydrofuran (20 ml), and stirred at 0° C. for 1 hour. The reaction mixture was extracted with ethyl acetate, and the extract was washed with water, dried and concentrated. The oily residue (2.4 g) was purified by column chromatography on silica gel eluting with a mixture of chloroform and methanol (20:1), and then recrystallized from ethanol to give colorless crystals of N-methyl-5-(4-fluorophenyl)-4-[4-(methylsulfonyl)phenyl]thiophene-2-sulfonamide (1.1 g).

mp: 199°–201° C.

IR (Nujol): 3300, 1600, 1510 $cm^{-1}$

NMR (DMSO-$d_6$, δ): 2.63 (3H, s), 3.25 (3H, s), 7.2–8.0 (9H, m)

Mass (m/z): 425 ($M^+$)

The following compound (Example 54) was obtained according to a similar manner to that of Example 53.

EXAMPLE 54

N,N-Dimethyl-5-(4-fluorophenyl)-4-[4-(methylsulfonyl)phenyl]thiophene-2-sulfonamide mp: 189°–191° C.

IR (Nujol): 1600, 1535, 1510 $cm^{-1}$

NMR (DMSO-$d_6$, δ): 2.79 (6H, s), 3.25 (3H, s), 7.2–8.0 (9H, m)

Mass (m/z): 439 ($M^+$)

EXAMPLE 55

A mixture of 5-(bromoacetyl)-2-(4-fluorophenyl)-3-[4-(methylsulfonyl)phenyl]thiophene (2 g) and thiourea (0.61 g) in ethanol (80 ml) was refluxed for 30 minutes. The mixture was dissolved in chloroform, washed with an aqueous solution of sodium bicarbonate and water, dried, and concentrated. The residue was purified by column chromatography on silica gel eluting with a mixture of chloroform and acetone (10:1) to give pale yellow crystals to 5-(2-amino-4-thiazolyl)-2-(4-fluorophenyl)-3-[4-(methylsulfonyl)phenyl]thiophene (0.62 g).

mp: 243°–245° C.

IR (Nujol): 3450, 3300, 3150, 1630, 1600, 1535, 1500 $cm^{-1}$

NMR (DMSO-$d_6$, δ): 3.20 (3H, s), 6.97 (1H, s), 7.0–7.6 (7H, m), 7.86 (2H, d, J=8 Hz)

Mass (m/z): 430 ($M^+$)

The following compound (Example 56) was obtained according to a similar manner to that of Example 55.

EXAMPLE 56

2-(4-Fluorophenyl)-5-[2-(methylamino)-4-thiazolyl]-3-[4-(methylsulfonyl)phenyl]thiophene mp: 176°–180° C.

IR (Nujol): 3250, 1590, 1550, 1500 $cm^{-1}$

NMR (DMSO-$d_6$, δ): 2.85 (3H, d, J=6 Hz), 3.20 (3H, s), 6.9–8.0 (11H, m)

Mass (m/z): 444 ($M^+$)

EXAMPLE 57

A mixture of 5-acetyl-2-(4-fluorophenyl)-3-[4-(methylsulfonyl)phenyl]thiophene (1.8 g) and (triphenylphosphoranylidene)acetonitrile (3.2 g) in toluene (40 ml) was refluxed for 28 hours. The mixture was cooled and filtered. The filtrate was concentrated and the residue (4.2 g) was purified by column chromatography on silica gel eluting with a mixture of toluene and ethyl acetate (10:1). The obtained crystals (1.8 g) were recrystallized from ethanol to give colorless crystals of 3-{5-(4-fluorophenyl)-4-[4-(methylsulfonyl)phenyl]-2-thienyl}-2-butenenitrile (1.5 g).

mp: 150°–154° C.

IR (Nujol): 2200, 1590, 1545, 1505 $cm^{-1}$

NMR (DMSO-$d_6$, δ): 2.45 (3H, s), 3.24 (3H, s), 6.12 (1H, s), 7.2–8.0 (9H, m)

EXAMPLE 58

A mixture of 2-(4-fluorophenyl)-3-[4-(methylsulfonyl)phenyl]thiophene (5 g), acetic anhydride (4.3 ml) and sulfuric acid (0.97 ml) in dichloromethane (47 ml) was stirred at ambient temperature overnight. The mixture was concentrated to give a crude blue oil of 5-(4-fluorophenyl)-4-[4-(methylsulfonyl)phenyl]thiophene-2-sulfonic acid (10.5 g).

The following compounds (Examples 59-1) to 59-4)) were obtained according to a similar manner to that of Example 10.

EXAMPLE 59

1) N-{5-(4-Fluorophenyl)-4-[4-(methylsulfonyl)phenyl]-2-thenoyl}-N-methylglycine mp: 78°–82° C.

IR (Nujol): 1740, 1600, 1545 $cm^{-1}$

NMR (DMSO-$d_6$, δ): 3.24 (3H, s), 3.38 (3H, s), 4.19 (2H, s), 7.1–8.0 (9H, m), 12.9 (1H, s)

Mass (m/z): 447 ($M^+$), 359

2) 4-[4-(Methylsulfonyl)phenyl]-5-(4-nitrophenyl)thiophene-2-carboxylic acid mp: 188°–190° C. (dec.)

IR (Nujol): 1710, 1600, 1515 $cm^{-1}$

NMR (DMSO-$d_6$, δ): 3.25 (3H, s), 7.5–7.7 (4H, m), 7.90 (2H, d, J=8 Hz), 7.92 (1H, s), 8.23 (2H, d, J=8 Hz)

Mass (m/z): 403 ($M^+$)

3) 4-[4-(Methylthio)phenyl]-5-(4-nitrophenyl)thiophene-2-carboxylic acid mp: 190°–195° C. (dec.)

IR (Nujol): 1690, 1595, 1515 $cm^{-1}$

NMR (DMSO-$d_6$, δ): 2.47 (3H, s), 6.6–8.3 (9H, m)

Mass (m/z): 371 ($M^+$)

4) 5-(2-Fluorophenyl)-4-[4-(methylthio)phenyl]thiophene-2-carboxylic acid mp: 160°–163° C. (dec.)

IR (Nujol): 3400, 1680, 1590 $cm^{-1}$

NMR (DMSO-$d_6$, δ): 2.45 (3H, s), 7.1–7.6 (8H, m), 7.87 (1H, s), 13.3 (1H, s)

Mass (m/z): 344 ($M^+$)

EXAMPLE 60

A mixture of ethyl 5-[4-(N-formylmethylamino)phenyl]-4-[4-(methylsulfonyl)phenyl]thiophene-2-carboxylate (0.34 g) and sodium methoxide (0.13 g) in formamide (2 ml) was stirred at 100° C. for 2.5 hours. The mixture was poured into ice-water and the precipitates were collected to give 5-[4-(N-formylmethylamino)phenyl]-4-[4-(methylsulfonyl)phenyl]thiophene-3-carboxamide (0.3 g).

mp: 227°–230° C. (dec.)

IR (Nujol): 3450, 3350, 3200, 1660, 1605 cm$^{-1}$

NMR (CDCl$_3$, δ): 3.09 (3H, s), 3.33 (3H, s), 5.87 (2H, s), 7.1–8.0 (9H, m), 8.60 (1H, s)

Mass (m/z): 414 (M$^+$)

The following compounds (Examples 61-1) and 61-2)) were obtained according to a similar manner to that of Example 60.

EXAMPLE 61

1) 5-[4-(N-Formylmethylamino)phenyl]-4-[4-(methylthio)phenyl]thiophene-2-carboxamide mp: 165°–170° C. (dec.)

IR (Nujol): 3400, 1680, 1660, 1605 cm$^{-1}$

NMR (CDCl$_3$, δ): 2.49 (3H, s), 3.32 (3H, s), 6.06 (2H, s), 7.0–7.5 (8H, m), 7.53 (1H, s), 8.54 (1H, s)

2) 5-(2-Fluorophenyl)-4-[4-(methylthio)phenyl]thiophene-2-carboxamide mp: 135°–140° C.

IR (Nujol): 3400, 3200, 1660, 1605, 1515 cm$^{-1}$

NMR (DMSO-d$_6$, δ): 2.45 (3H, s), 7.1–7.8 (8H, m), 7.98 (1H, s)

Mass (m/z): 343 (M$^+$)

The following compounds (Examples62-1) to 62-5)) were obtained according to a similar manner to that of Example 27.

EXAMPLE 62

1) 5-Chloro-2-[4-(N-formylmethylamino)phenyl]-3-[4-(methylsulfinyl)phenyl]thiophene mp: 167°–170° C.

IR (Nujol): 1675, 1605, 1510 cm$^{-1}$ 2) 5-Bromo-2-[4-(N-formylmethylamino)phenyl]-3-[4-(methylsulfinyl)phenyl]thiophene mp: 168°–170° C.

IR (Nujol): 1675, 1605, 1515 cm$^{-1}$ 3) 5-Acetyl-2-[4-(N-formylmethylamino)phenyl]-3-[4-(methylsulfinyl)phenyl]thiophene mp: 145°–150° C.

IR (Nujol): 1680, 1660, 1600 cm$^{-1}$ 4) 5-[4-(N-Formylmethylamino)phenyl]-4-[4-(methylsulfinyl)phenyl]thiophene-2-carbonitrile mp: 185°–190° C. (dec.)

NMR (CDCl$_3$, δ): 2.77 (3H, s), 3.37 (3H, s), 7.1–7.7 (9H, m), 8.57 (1H, s)

5) 5-Acetyl-2-(4-methoxyphenyl)-3-[4-(methylsulfinyl)phenyl]thiophene mp: 175°–178° C. (dec.)

IR (Nujol): 1660, 1610, 1515 cm$^{-1}$

NMR (CDCl$_3$, δ): 2.59 (3H, s), 2.76 (3H, s), 3.82 (3H, s), 6.8–7.7 (8H, m), 7.71 (1H, s)

Mass (m/z): 370 (M$^+$), 355

EXAMPLE 63

A mixture of acetic anhydride (1.1 g) and formic acid (0.8 g) was heated at 50° C. for 30 minutes. To the mixture was added ethyl 5-(4-aminophenyl)-4-[4-(methylsulfonyl)phenyl]thiophene-2-carboxylate (0.5 g). The mixture was stirred at ambient temperature for 4 hours and poured into ice-water. The precipitates were collected, washed with water, and dried in vacuo to give ethyl 5-[4-(formylamino)phenyl]-4-[4-(methylsulfonyl)phenyl]thiophene-2-carboxylate (0.38 g).

mp: 175°–180° C. (dec.)

IR (Nujol): 3350, 1705, 1690, 1600 cm$^{-1}$

NMR (DMSO-d$_6$, δ): 1.30 (3H, t, J=7 Hz), 3.25 (3H, s), 4.34 (2H, q, J=7 Hz), 7.2–8.0 (9H, m), 8.31 (1H, s), 10.4 (1H, s)

Mass (m/z): 429 (M$^+$)

The following compounds (Examples 64-1) to 64-5)) were obtained according to a similar manner to that of Example 63.

EXAMPLE 64

1) 5-Bromo-2-[4-(formylamino)phenyl]-3-[4-(methylsulfonyl)phenyl]thiophene mp: 145°–150° C. (dec.)

IR (Nujol): 3300, 1690, 1600, 1515 cm$^{-1}$

NMR (CDCl$_3$, δ): 3.08 (3H, s), 7.0–7.9 (9H, m), 8.40 (1H, s)

Mass (m/z): 436 (M$^+$)

2) 5-Chloro-2-[4-(formylamino)phenyl]-3-[4-(methylthio)phenyl]thiophene

IR (Nujol): 1675, 1600, 1515 cm$^{-1}$ 3) 5-Bromo-2-[4-(formylamino)phenyl]-3-[4-(methylthio)phenyl]thiophene mp: 150°–160° C. (dec.)

IR (Nujol): 1690, 1600 cm$^{-1}$

Mass (m/z): 405, 403

4) 5-Acetyl-2-[4-(formylamino)phenyl]-3-[4-(methylthio)phenyl]thiophene

IR (Film): 3250, 1695, 1660, 1605, 1515 cm$^{-1}$

5) Ethyl 5-[4-(formylamino)phenyl]-4-[4-(methylthio)phenyl]thiophene-2-carboxylate NMR (DMSO-d$_6$, δ): 1.35 (3H, t, J=7 Hz), 2.47 (3H, s), 4.33 (2H, q, J=7 Hz), 7.1–7.7 (8H, m), 7.82 (1H, s), 8.30 (1H, s), 10.4 (1H, s)

Mass (m/z): 397 (M$^+$)

EXAMPLE 65

Sodium hydride (60%; 40 mg) was added to an ice-cooled solution of ethyl 5-[4-(formylamino)phenyl]-4-[4-(methylsulfonyl)phenyl]thiophene-2-carboxylate (0.35 g) in N,N-dimethylformamide (10 ml). The mixture was stirred at ambient temperature for 30 minutes, and to the resulting mixture was added methyl iodide (0.23 g) at 5° C. The mixture was stirred at ambient temperature for 1.5 hours and poured into ice-water. The precipitates were collected, washed with water, and dried in vacuo to give ethyl 5-[4-(N-formylmethylamino)phenyl]-4-[4-(methylsulfonyl)phenyl]thiophene-2-carboxylate (0.34 g).

mp: 190°–195° C. (dec.)

IR (Nujol): 1715, 1680, 1605 cm$^{-1}$

NMR (CDCl$_3$, δ): 1.42 (3H, t, J=7 Hz), 3.09 (3H, s), 3.33 (3H, s), 4.40 (2H, q, J=7 Hz), 7.1–8.0 (9H, m), 8.57 (1H, s)

Mass (m/z): 443 (M$^+$)

The following compounds (Examples 66-1) to 66-5)) were obtained according to a similar manner to that of Example 65.

EXAMPLE 66

1) 5-Bromo-2-[4-(N-formylmethylamino)phenyl]-3-[4-(methylsulfonyl)phenyl]thiophene mp: 188°–191° C. (dec.)

IR (Nujol): 1680, 1600, 1510 cm$^{-1}$

NMR (CDCl$_3$, δ): 3.12 (3H, s), 3.32 (3H, s), 7.0–7.5 (7H, m), 7.87 (2H, d, J=8 Hz), 8.54 (1H, s)

2) 5-Chloro-2-[4-(N-formylmethylamino)phenyl]-3-[4-(methylthio)phenyl]thiophene mp: 165°–170° C. (dec.)
IR (Nujol): 1680, 1605, 1510 cm$^{-1}$
3) 5-Bromo-2-[4-(N-formylmethylamino)phenyl]-3-[4-(methylthio)phenyl]thiophene
mp: 150°–155° C. (dec.)
IR (Nujol): 1685, 1600 cm$^{-1}$
Mass (m/z): 419, 417
4) 5-Acetyl-2-[4-(N-formylmethylamino)phenyl]-3-[4-(methylthio)phenyl]thiophene
IR (Nujol): 1695, 1660, 1600, 1540 cm$^{-1}$
Mass (m/z): 381 (M$^+$)
5) Ethyl 5-[4-(N-formylmethylamino)phenyl]-4-[4-(methylthio)phenyl]thiophene-2-carboxylate
mp: 158°–160° C.
IR (Nujol): 1680, 1605 cm$^{-1}$
NMR (CDCl$_3$, δ): 1.41 (3H, t, J=7 Hz), 2.48 (3H, s), 3.36 (3H, s), 4.40 (2H, q, J=7 Hz), 7.0–7.6 (8H, m), 7.81 (1H, s), 8.55 (1H, s)
Mass (m/z): 411 (M$^+$)

EXAMPLE 67

A mixture of 5-[4-(N-formylmethylamino)phenyl]-4-[4-(methylsulfonyl)phenyl]thiophene-2-carboxamide (0.3 g) and methanesulfonyl chloride (0.5 g) in pyridine (1.5 ml) was stirred at 50° C. for 3 hours. The mixture was poured into dilute hydrochloric acid. The precipitates were collected and washed with water to give 5-[4-(N-formylmethylamino)phenyl]-4-[4-(methylsulfonyl)phenyl]thiophene-2-carbonitrile (0.25 g).
mp: 190°–195° C. (dec.)
IR (Nujol): 2220, 1675, 1600, 1510 cm$^{-1}$
NMR (CDCl$_3$, δ): 3.10 (3H, s), 3.34 (3H, s), 7.1–8.0 (9H, m), 8.58 (1H, s)
Mass (m/z): 396 (M$^+$)

The following compound (Example 68) was obtained according to a similar manner to that of Example 67.

EXAMPLE 68

5-[4-(N-Formylmethylamino)phenyl]-4-[4-(methylthio)phenyl]thiophene-2-carbonitrile mp: 155°–160° C. (dec.)
IR (Nujol): 2230, 1680, 1605 cm$^{-1}$
NMR (CDCl$_3$, δ): 2.50 (3H, s), 3.32 (3H, s), 7.0–7.4 (8H, m), 7.62 (1H, s), 8.56 (1H, s)
Mass (m/z): 364 (M$^+$)

EXAMPLE 69

A mixture of 5-[4-(N-formylmethylamino)phenyl]-4-[4-(methylsulfonyl)phenyl]thiophene-2-carbonitrile (2.2 g) and concentrated hydrochloric acid (13 ml) in methanol (60 ml) and tetrahydrofuran (40 ml) was stirred at ambient temperature for 2.5 hours. The mixture was concentrated and the residue was triturated in a sodium bicarbonate solution to give a powder. The crude powder was purified by column chromatography on silica gel eluting with a mixture of toluene and ethyl acetate (4:1) to give a yellow powder of 5-[4-(methylamino)phenyl]-4-[4-(methylsulfonyl)phenyl]thiophene-2-carbonitrile (1.4 g).
mp: 188°–190° C.
IR (Nujol): 3450, 2220, 1610, 1520 cm$^{-1}$
NMR (CDCl$_3$, δ): 2.86 (3H, s), 3.08 (3H, s), 6.50 (2H, d, J=8 Hz), 7.04 (2H, d, J=8 Hz), 7.45 (2H, d, J=8 Hz), 7.60 (1H, s), 7.87 (2H, d, J=8 Hz)
Mass (m/z): 368 (M$^+$)

The following compounds (Examples 70-1) to 70-5)) were obtained according to a similar manner to that of Example 69.

EXAMPLE 70

1) 5-Bromo-2-[4-(methylamino)phenyl]-3-[4-(methylsulfonyl)phenyl]thiophene
mp: 180°–182° C.
IR (Nujol): 3450, 1610, 1595, 1520 cm$^{-1}$
NMR (CDCl$_3$, δ): 2.84 (3H, s), 3.06 (3H, s), 6.49 (2H, d, J=8 Hz), 7.04 (2H, d, J=8 Hz), 7.14 (1H, s), 7.42 (2H, d, J=8 Hz), 7.82 (2H, d, J=8 Hz) Mass (m/z): 423, 421
2) 5-Chloro-2-[4-(methylamino)phenyl]-3-[4-(methylsulfinyl)phenyl]thiophene
mp: 150°–155° C. (dec.)
IR (Nujol): 3350, 1610, 1515 cm$^{-1}$
NMR (CDCl$_3$, δ): 2.75 (3H, s), 2.84 (3H, s), 6.50 (2H, d, J=8 Hz), 7.0–7.6 (7H, m)
3) 5-Bromo-2-[4-(methylamino)phenyl]-3-[4-(methylsulfinyl)phenyl]thiophene
mp: 160°–164° C. (dec.)
Mass (m/z): 407, 405
4) 5-Acetyl-2-[4-(methylamino)phenyl]-3-[4-(methylsulfinyl)phenyl]thiophene
mp: 180°–185 ° C. (dec.)
IR (Nujol): 3350, 1650, 1610, 1515 cm$^{-1}$
Mass (m/z): 369 (M$^+$)
5) 5-[4-(Methylamino)phenyl]-4-[4-(methylsulfinyl)phenyl]thiophene-2-carbonitrile
mp: 140°–143° C.
IR (Nujol): 3350, 2225, 1610, 1515 cm$^{-1}$
NMR (CDCl$_3$, δ): 2.75 (3H, s), 2.85 (3H, s), 4.0 (1H, m), 6.49 (2H, d, J=8 Hz), 7.0–7.7 (7H, m)
Mass (m/z): 352 (M$^+$)

EXAMPLE 71

A mixture of 5-(4-fluorophenyl)-4-[4-(methylsulfonyl)phenyl]thiophene-2-carbonitrile (3.1 g), sodium azide (1.3 g) and ammonium chloride (1.5 g) in N,N-dimethylformamide (30 ml) was stirred at 120° C. for 24 hours. The mixture was poured into ice-water, and the resulting mixture was acidified. The precipitates were collected and recrystallized from ethanol to give crystals of 2-(4-fluorophenyl)-3-[4-(methylsulfonyl)phenyl]-5-(5-tetrazolyl)thiophene (0.9 g).
mp: 200°–205° C. (dec.)
NMR (DMSO-d$_6$, δ) 3.27 (3H, s), 7.2–7.6 (6H, m), 7.93 (2H, d, J=8 Hz), 7.95 (1H, s)
Mass (m/z): 400 (M$^+$), 372

We claim:
1. A compound of the formula:

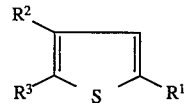

wherein
R$^1$ is bromo; cyano; lower alkyl substituted with a substituent selected from the group consisting of hydroxy, amino, acylamino, lower alkylamino, lower alkyl(acyl)amino, acyl, hydroxyimino and lower alkoxyimino; lower alkyl substituted with halogen; lower alkenyl optionally substituted with cyano; acyl; nitro; amino optionally substituted with substituent(s) selected from the group consisting of acyl and lower alkylsulfonyl; sulfo; sulfamoyl optionally substituted with lower alkyl, hydroxy; or a heterocyclic group other than thienyl and tetrazolyl substituted with substituent(s) selected from the group consisting of hydroxy, oxo, amino and lower alkylamino;

$R^2$ is aryl substituted with substituent(s) selected from the group consisting of halogen, lower alkoxy, lower alkylthio, lower alkylsulfinyl, lower alkylsulfonyl, nitro, amino, sulfamoyl and lower alkylsulfonylamino; and $R^3$ is aryl substituted with substituent(s) selected from the group consisting of halogen, lower alkoxy, lower alkylthio, lower alkylsulfinyl, lower alkylsulfonyl, nitro, amino, lower alkylamino, acylamino, lower alkyl(acyl)amino, lower alkylsulfonylamino and sulfamoyl; provided that $R^3$ is aryl substituted with substituent(s) selected from the group consisting of amino, mono(lower)alkylamino, acylamino, lower alkyl(acyl)amino and sulfamoyl when $R^1$ is bromo or cyano, and pharmaceutically acceptable salts thereof.

2. A pharmaceutical composition comprising a compound of claim 1, as an active ingredient, in association with a pharmaceutically acceptable, substantially nontoxic carrier or excipient.

3. A compound according to claim 1:
wherein
$R^1$ is bromo; lower alkyl substituted with a substituent selected from the group consisting of hydroxy, amino, lower alkylamino and acyl; lower alkyl substituted with halogen; acyl; nitro; amino optionally substituted with lower alkylsulfonyl; sulfamoyl optionally substituted with lower alkyl; hydroxy; or a heterocyclic group substituted with lower alkylamino.

4. A compound according to claim 3:
wherein $R^1$ is bromo; lower alkyl substituted with halogen or lower alkylamino; acyl; nitro; sulfamoyl substituted with lower alkyl; $R^2$ is aryl substituted with lower alkylsulfonyl, lower alkylsulfinyl or halogen; and $R^3$ is aryl substituted with lower alkylsulfonyl, lower alkylamino, acylamino, lower alkoxy or halogen;

provided that $R^3$ is aryl substituted with mono(lower)alkylamino or acylamino when $R^1$ is bromo.

5. A compound according to claim 4:
wherein $R^1$ is lower alkyl substituted with halogen or lower alkylamino, $R^2$ is phenyl substituted with lower alkylsulfonyl and $R^3$ is phenyl substituted with halogen.

6. A method for therapeutic treatment of inflammatory conditions, various pains, or collagen diseases which comprises administering an effective amount of a compound of claim 1 to human beings or animals.

7. A compound according to claim 4,
wherein $R^1$ is bromo,
$R^2$ is aryl substituted with lower alkylsulfinyl, and
$R^3$ is aryl substituted with mono(lower)alkylamino.

8. A compound of claim 7, which is 5-bromo-2-[4-(methylamino)phenyl]-3-[4-(methylsulfinyl)phenyl]thiophene.

* * * * *